US009925298B2

(12) United States Patent
Das et al.

(10) Patent No.: US 9,925,298 B2
(45) Date of Patent: Mar. 27, 2018

(54) POROUS POLYMER SCAFFOLD USEFUL FOR TISSUE ENGINEERING IN STEM CELL TRANSPLANTATION

(71) Applicant: COUNCIL OF SCIENTIFIC & INDUSTRIAL RESEARCH, New Delhi (IN)

(72) Inventors: Amitava Das, Andhra Pradesh (IN); Pratyay Basak, Andhra Pradesh (IN); Ramasatyaveni Geesala, Andhra Pradesh (IN); Nimai Bar, Andhra Pradesh (IN); Neha Raghuvir Dhoke, Andhra Pradesh (IN); Komal Kaushik, Andhra Pradesh (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 0 days.

(21) Appl. No.: 15/336,187

(22) Filed: Oct. 27, 2016

(65) Prior Publication Data

US 2017/0112960 A1    Apr. 27, 2017

(30) Foreign Application Priority Data

Oct. 27, 2015    (IN) .......................... 3470/DEL/2015

(51) Int. Cl.
*A61L 27/18*      (2006.01)
*A61K 47/44*     (2017.01)
(Continued)

(52) U.S. Cl.
CPC ............... *A61L 27/18* (2013.01); *A61L 27/54* (2013.01); *A61L 27/56* (2013.01); *C08G 18/10* (2013.01);
(Continued)

(58) Field of Classification Search
CPC .......... A61L 27/18; A61L 27/54; A61L 27/56; C08G 18/10; C08G 18/14; C08G 18/4825;
(Continued)

(56) References Cited

U.S. PATENT DOCUMENTS

| 4,826,945 A | 5/1989 | Cohn et al. ..................... 528/76 |
| 5,099,060 A | 3/1992 | Kohn et al. ..................... 560/40 |

(Continued)

FOREIGN PATENT DOCUMENTS

WO    WO 94/025079    11/1994

OTHER PUBLICATIONS

Divakaran et al. (Polym Int 2015;64:397-404 first published Sep. 22, 2014).*

(Continued)

*Primary Examiner* — Ernst V Arnold
(74) *Attorney, Agent, or Firm* — Norton Rose Fulbright US LLP

(57) ABSTRACT

The present invention relates to the synthesis of porous polymer scaffold from polyethyleneglycol-polyurethane having castor oil linkages under controlled conditions and their use as stem cell delivery vehicles thereby accelerating the tissue regeneration process. The present invention further studies the biodegradability, stability and biocompatibility of porous polymer scaffolds in various cell lines and primary bone marrow stem cells. Particularly the present invention further relates to the physio-chemical characterization of the porous polymer scaffolds.

20 Claims, 45 Drawing Sheets

Figure 1A:
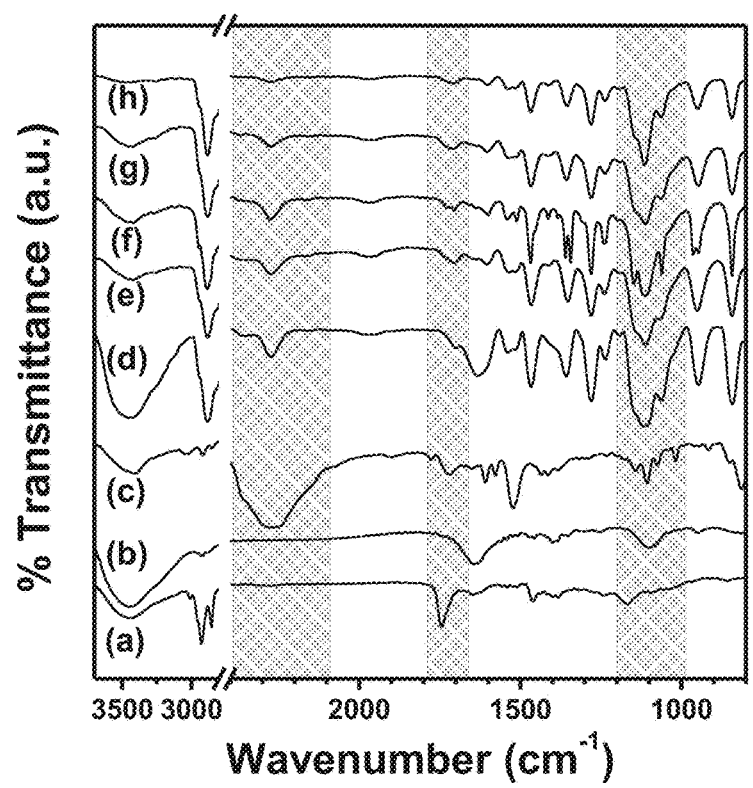

(51) Int. Cl.
| | |
|---|---|
| C12N 5/00 | (2006.01) |
| A61L 27/56 | (2006.01) |
| A61L 27/54 | (2006.01) |
| C08G 18/10 | (2006.01) |
| C08G 18/48 | (2006.01) |
| C08G 18/08 | (2006.01) |
| C08J 9/26 | (2006.01) |
| C08L 71/02 | (2006.01) |
| C08L 75/08 | (2006.01) |

(52) U.S. Cl.
CPC ......... *C08G 18/14* (2013.01); *C08G 18/4825* (2013.01); *C08J 9/26* (2013.01); *C08L 71/02* (2013.01); *C08L 75/08* (2013.01); *C12N 5/0068* (2013.01); *C08J 2201/0462* (2013.01); *C08J 2207/10* (2013.01); *C08J 2371/02* (2013.01); *C08J 2375/08* (2013.01); *C08L 2203/02* (2013.01); *C08L 2205/04* (2013.01); *C12N 2533/30* (2013.01); *C12N 2537/10* (2013.01)

(58) Field of Classification Search
CPC ............ C08J 2201/0462; C08J 2207/10; C08J 2371/02; C08J 2375/08; C08J 9/26; C08L 2203/02; C08L 2205/04; C08L 71/02
See application file for complete search history.

(56) References Cited

U.S. PATENT DOCUMENTS

| | | | |
|---|---|---|---|
| 5,198,507 A | 3/1993 | Kohn et al. .................... 525/432 |
| 5,514,378 A | 5/1996 | Mikos et al. .................. 424/425 |
| 5,686,091 A | 11/1997 | Leong et al. ................. 424/426 |
| 5,723,508 A | 3/1998 | Healy et al. .................... 521/61 |
| 6,103,255 A | 8/2000 | Levene et al. ................ 424/426 |
| 6,485,521 B1 | 11/2002 | Say et al. .................... 623/23.55 |
| 6,626,950 B2 | 9/2003 | Brown et al. .............. 623/23.72 |
| 6,696,575 B2 | 2/2004 | Schmidt et al. .............. 548/524 |
| 6,743,232 B2 | 6/2004 | Overaker et al. ............... 606/72 |
| 6,852,330 B2 | 2/2005 | Bowman et al. ............. 424/426 |
| 7,101,857 B2 | 9/2006 | Sung et al. ...................... 514/26 |
| 7,338,517 B2 | 3/2008 | Yost et al. ...................... 623/1.1 |
| 9,243,102 B2* | 1/2016 | Rashid ............... C08G 18/4833 |
| 2010/0099758 A1* | 4/2010 | Martin ................... A61K 31/30 514/495 |

OTHER PUBLICATIONS

Jililian et al. (Polym Int 2008;57:1385-1394).*
Calvino-Casilda et al. (J. Phys. Chem. B 2008;112:2809-2817).*
Du et al. (Materials Science Forum 2013;761:141-144). (Year: 2013).*
Anand, et al., "Bioavailability of Curcumin: Problems and Promises," *Molecular Pharmaceutics*, 2007; 4(6): 807-818.
Archana et al., "Development of constrained tamoxifen mimics and their antiproliferative properties against breast cancer cells," *Bioorganic and Medicinal Chemistry Letters*, 2015; 25: 680-684.
Atala, Anthony, Robert Lanza, Robert Nerem, James A. Thomson, eds., *Principles of Regenerative Medicine*, Academic Press: 2007, Abstract Only.
Baber et al., "Liquid-Liquid equilibrium of the castor oil + soybean oil + hexane ternary system" *J. Chem. Eng. Data*, 2002; 47: 1502-1505.
Basak et al., "Investigations on the Mechanisms of Ionic Conductivity in PEO-PU/PAN Semi-interpenetrating Polymer Network-Salt Complex Polymer Electrolytes: An Impedance Spectroscopy Study," *J. Phys. Chem.* 2005; 109: 1174-1182.
Basak et al., "Poly(Ethylene Oxide)-Polyurethane/Poly(Acrylonitrile) Semi-Interpenetrating Polymer Networks For Solid Polymer Electrolytes: Vibrational Spectroscopic Studies In Support Of Electrical Behavior," *European Polymer Journal*, 2004; 40: 1155-1162.
Basak et al., "Thermo-Mechanical Porperties Of PEO-PU/PAN Semi-Interpenetrating Polymer Networks And Their LiClO$_4$ Salt-Complexes" *Journal of Macromolecular Science, Part A: Pure and Applied Chemistry*, 2006; 43: 369-382.
Biermann et al., "New syntheses with oils and fats as renewable raw materials for the chemical industry," *Agnew. Chem. Int. Ed*. 2000; 39: 2206-2224.
Bryan et al., "Reactive oxygen species (ROS)—a family of fate deciding molecules pivotal in constructive inflammation and wound healing," *European Cells and Materials* 2012; 24: 249-265.
Case et al., "Oxidative stress impairs endothelial progenitor cell function," *Antioxidants and Redox Signaling*, 2008; 10(11):1895-1907.
Chen et al., "Homing of endogenous stem/progenitor cells for in situ tissue regeneration: promises, strategies, and translational perspectives," *Biomaterials*, 2011; 32: 3189-3209.
Crisanti et al., "Novel methods for delivery of cell based therapies," *J. Surg. Res*. 2008; 146(1): 3-10.
Das et al., "Disruption of an SP2/KLF6 repression complex by SHP is required for Farnesoid X receptor-induced endothelial cell migration," *J. Biol. Chem*. 2006; 281(51): 39105-39113.
Dhandayuthapani et al., "Polymeric scaffolds in tissue engineering application: a review," *International Journal of Polymer Science*, 2011; 2011: 1-19.
Eming et al., "Inflammation in wound repair: molecular and cellular mechanisms," *Journal of Investigative Dermatology*, 2007; 127: 514-525.
Fang et al., "Free Radicals, Antioxidants, and Nutrition," *Nutrition*, 2002; 18(10): 872-879.
Gomes et al., "TGF-β1 modulates the homeostasis between MMPs and MMP inhibitors through p38 MAPK and ERK1/2 in highly invasive breast cancer cells," *BMC Cancer*, 2012; 12(26): 1-15.
Guan et al., "Biodegradable poly(ether ester urethane)urea elastomers based on poly(ether ester) triblock copolymers and putrescine: synthesis, characterization and cytocompatibility," *Biomaterials*, 2004; 25: 85-96.
Gunatillake et al., "Biodegradable synthetic polymers for tissue engineering," *European Cells and Materials*, 2003; 5: 1-16.
Havlik et al., "Vitamin E and wound healing," *Plastic and Reconstructive Surgery*, 1997; 1901-1902.
Holy et al., "Engineering three-dimensional bone tissue in vitro using biodegradable scaffolds: investigating initial cell-seeding density and culture period," *Journal of Biomedical Materials Research*, 1999; 51(3): 376-382.
Ismail et al., "Antioxidant enzyme activities in hepatic tissue from children with chronic cholestatic liver disease," *The Saudi Journal of Gastroenterology*, 2010; 16(2): 90-94.
Ismail et al., "Glutathione peroxidase, superoxide dismutase and catalase activities in children with chronic hepatitis," *Advances in Bioscience and Biotechnology* 2012; 3: 972-977.
Jensen, E. "Quantitative analysis of histological staining and fluorescence using ImageJ," *The Anatomical Record*, 2013; 296: 378-381.
Lau et al., "Cellular and molecular mechanisms of accelerated fracture healing by COX2 gene therapy. Studies in mouse model of multiple fractures," *Bone*, 2013; doi: 10.1016/j.bone.2013.01.003, 40 pages.
Liao et al., "Lumbar spinal fusion with a mineralized collagen matrix and rhBMP-2 in a rabbit model," *SPINE*, 2003; 28(17): 1954-1960.
Lin et al., "An in vivo study on the biocompatibility of a bioresorbable Poly(L-lactide-co-glycolide) Pin for Bone Fixation," *J. Med Biol. Eng*. 2001; 21(4): 233-242.
Lin et al., "Impaired Wound Healing With Defective Expression Of Chemokines And Recruitment Of Myeloids Cells In TLR3-Deficient Mice," *Journal of Immunology*, 2011; 186: 3710-3717.
Makadia et al., "Poly Lactic-co-Glycolic Acid (PLGA) as biodegradable controlled drug delivery carrier," *Polymers*, 2011; 3: 1377-1397.

(56) References Cited

OTHER PUBLICATIONS

Newton et al., "Macrophages Restrain Contraction Of An In Vitro Wound Healing Model," *Inflammation*, 2004; 28(4): 207-214.

Noiseux et al., "Mesenchymal stem cells overexpressing akt dramatically repair infarcted myocardium and improve cardiac function despite infrequent cellular fusion or differentiation," *Molecular Therapy*, 2006; 14(6): 840-850.

Park et al., "Biodegradable polymers for microencapsulation of drugs," *Molecules*, 2005; 10: 146-161.

Patrick et al., "NAD(P)H: quinone oxidoreductase 1 protects bladder epithelium against painful bladder syndrome in mice," *Free Radical Biology and Medicine*, 2012; 53: 1886-1893.

Rahman et al., "Oxidative stress and human health," *Advances in Bioscience and Biotechnology*, 2012; 3: 997-1019.

Rasik et al., "Antioxidant status in delayed healing type of wounds," *Int. J. Exp. Path*, 2000; 81: 257-263.

Sabir et al., "A review on biodegradable polymeric materials for bone tissue engineering applications," *J. Mater. Sci.* 2009; 44: 5713-5724.

Schafer and Werner, "Oxidative Stress in Normal and Impaired Wound Repair," *Pharmacological Research*, 2008; 58: 165-171.

Seal et al., "Polymeric biomaterials for tissue and organ regeneration," *Materials Science and Engineering*, 2001; 34: 147-230.

Shareef et al., "Investigation of podophyllotoxin esters as potential anticancer agents: Synthesis, biological studies and tubulin inhibition properties," *European Journal of Medicinal Chemistry*, 2015; 89: 128-137.

Storz et al., "FOXO3a promotes tumor cell invasion through the induction of matrix metalloproteinases," *Molecular and Cellular Biology*, 2009; 29(18): 4906-4917.

Strober, W., "Trypan Blue Exclusion Test of Cell Viability," *Current Protocols in Immunology*, 1997, A.3B.1-A.3B.2.

Tan et al., "Cyr61 increases migration and MMP-13 expression via $\alpha v \beta 3$ integrin, FAK, ERK, and AP-1-dependent pathway in human chondrosarcoma cells," *Carcinogenesis*, 2009; 30(2): 258-268.

Vichai et al., "Sulforhodamine B colorimetric assay for cytotoxicity screening," *Nature Protocols* 2006; 1(3): 1112-1116.

Wang et al., "The mouse excisional wound splinting model, including applications for stem cell transplantation," *Nature Protocol*, 2013; 8(2): 302-309.

West et al., "Polymeric biomaterials with degradation sites for proteases involved in cell migration," *Macromolecules*, 1999; 32: 241-244.

Wu et al., "Concise Review: Bone marrow-derived stem/progenitor cells in cutaneous repair and regeneration," *Stem Cells* 2010; 28: 905-915.

Wu et al., "Mesenchymal stem cells enhance wound healing through differentiation and angiogenesis," *Stem Cells*, 2007; 26: 2648-2659.

Yeganeh et al., "Preparation and properties of novel biodegradable polyurethane networks based on castor oil and poly(ethylene glycol)," *Polymer Degradation and Stability*, 2007; 92: 480-489.

\* cited by examiner

|  | MDA-MB-231 | SK-Hep1 | BMSCs |
|---|---|---|---|
| Cells | 100±0.17 | 100±0.1 | 100±0.13 |
| Cells+ PEG+PU | 105±0.21 | 124.8±0.15 | 99±0.140 |

POROUS POLYMER SCAFFOLD USEFUL FOR TISSUE ENGINEERING IN STEM CELL TRANSPLANTATION

PRIORITY CLAIM

The present application claims priority to Indian Application No. 3470/DEL/2015 filed Oct. 27, 2015, which is incorporated herein by reference.

FIELD OF THE INVENTION

The invention relates to the synthesis of biodegradable porous polymer scaffold from polyethyleneglycol-polyurethane (PEG-PU) under controlled conditions and its use as cell delivery vehicles of stem cells thereby accelerating the tissue regeneration processes, in particular to chronic wounds, diseases related to impaired neo-vascularization and ROS-induced degenerative diseases.

BACKGROUND OF THE INVENTION

Chronic wound remains as a constant challenge for patients with diabetes or treated with immunosuppressive drugs, chemo- and radio-therapies. Mechanisms underlying poor wound healing are still unclear (see, Fang, et al., Nutrition. 2002, 18, pp. 872-879). Wound healing is generally characterized by haemostasis, inflammation, migration and proliferation of fibroblasts, endothelial and epithelial cells, deposition of connective tissue such as collagen, followed by angiogenesis and re-epithelialization. A complex cascade of regulated steps with complications of persistent inflammation, fibroblast dysfunction and impaired angiogenesis often leads to morbidity and mortality.

An increased level of oxygen free radicals and other reactive oxygen species (ROS) like $H_2O_2$ as by-products along with pro-inflammatory mediators at wound site, play a crucial role in impaired wound healing. Hence, antioxidants that help in maintaining a balance by metabolizing/reducing the ROS levels at wound site could be an effective strategy to ameliorate cellular dysfunction.

Apart from pharmacological approaches such as curcumin, a known antioxidant and anti-inflammatory agent with poor bioavailability issues (see, Anand, P et al., Mol. Pharmaceut., 2007, 4, pp. 807-818), conventional surgical treatments like skin autograft and allograft, artificial skin embedded with epidermal/fibroblastic cells has their own disadvantages such as limited tissue availability, high cost, immune-rejection and prolonged time of healing. To overcome these limitations, bone marrow derived stem cells can be potential candidates for cell transplantation therapies (see, Schafer, M et al., Pharmacol. Res. 2008, 58, pp. 165-171). Transplantation of stem cells isolated from bone marrow has been used for tissue regeneration, albeit with a limitation of low bio-availability upon systemic administration (see, Chen, F. M et al., Biomaterials 2011, 32, pp. 189-209). Nevertheless, this strategy, has also met with limited success owing to enhanced ROS (Reactive oxygen species) levels at injury site that impairs the function of stem cells transplanted at chronic wounds (see, Case, J. et al Antioxid. Redox Signal. 2008, 10, pp. 1895-1907). Thus, a delivery mechanism of stem cells on-site coupled with capabilities of ROS levels diminution could be an improved and novel therapeutic strategy for chronic wounds.

To protect transplanted cells, use of biodegradable scaffolds/bio-polymers as carriers of cells to the site of tissue injury could be an efficient therapeutic approach. Synthetic biodegradable polymers have proven to be highly potent in many biomedical applications. In tissue engineering, these polymers can be used as temporary scaffolds and as surgical devices or implants for drug and gene delivery (see, Crisanti, C. M. et al., J. Surg. Res. 2008, 146, pp. 3-10). Polymer material should be processed into thin films with a controlled thickness, biocompatible, allow attachment/proliferation of anchorage-dependent cells, and bio-degradable over a desired period of time after implantation (see, Seal B. L et al., Mater. Sci. Eng: Reports 2001, 34, pp. 147-230; WO1994025079A1, U.S. Pat. No. 5,723,508, U.S. Pat. No. 5,686,091, U.S. Pat. No. 5,514,378, U.S. Pat. No. 5,198,507, U.S. Pat. No. 5,099,060, U.S. Pat. No. 4,826,945, U.S. Pat. No. 6,103,255A).

Currently, aliphatic polyesters prepared from lactic and glycolic acids are the most versatile and widely used synthetic biodegradable polymers as suture material, scaffolds for soft and hard tissue repair as well as drug carriers. (See, U.S. Pat. No. 6,626,950, U.S. Pat. No. 6,485,521, U.S. Pat. No. 6,696,575, U.S. Pat. No. 6,696,575, U.S. Pat. No. 6,743,232, U.S. Pat. No. 6,852,330, U.S. Pat. No. 7,101,857, U.S. Pat. No. 7,338,517, Sabir, M. I et al., J. Mater. Sci. 2009, 44, pp. 5713-5724.; Chi-KuangFeng, Y. L et al., J. Med. Biol. Eng. 2001, 21, pp. 233-242; Liao, S. S et al., J Bioact. Compat. Polym. 2004, 19, pp. 117-130). However, contradictory reports exist regarding the biocompatible properties of these PLA-PGA-based biopolymers, (see, Makadia, H. K et al., Polymers 2011, 3, pp. 1377-1397; Dhandayuthapani, B et al., Int. J Polym. Sci. 2011, 9) such as, release of acidic by-products, poor processability, loss of mechanical properties at an early time point during degradation that often causes systemic and/or local reactions along with adverse responses (see, Gunatillake, P. A et al., Eur. Cells Mater. 2003, 5, pp. 1-16). Among all polymers widely studied, polyurethanes offer several advantages in designing biodegradable scaffolds. In this context interpenetrating polymer network approach provides several opportunities to tailor the polymeric architecture for tuning dimensional, thermal and mechanical stability along with matrix homogeneity and low degree of crystallinity (see, Park, J. H et al., Molecules 2005, 10, pp. 146-161.; Atala, A et al., Principles of Regen. Med. 2011, p. 1436). However, the mechanisms of cell penetration into these polyurethane scaffolds are lacking in literature.

Biomaterials synthesized using polyurethanes can be made biocompatible, biodegradable with wide range of chemical linkages that help in targeted delivery to specific tissue microenvironment. Synthetically, hydroxyl terminated polymers as starting material for polyurethanes like polycaprolactone, polylactides, polygylcolides, polyethyleneglycols, polyalkyleneadipate, etc. have shown promise as scaffold materials with the polyol based soft segments being hydrolytically degradable (See, Lee, S. I. et al., Biomaterials 2004, 25, pp. 85-96). While biodegradation in polyurethanes can be easily achieved by incorporating hydrolysable moieties like esters in the polymeric chain, control on occasional cytotoxicity of cleaved fragments post-degradation remains the key area of concern and challenge.

To retain structural integrity, porous polyurethane scaffolds are synthesized in network form with intermittent cross-links aiding a 3-dimensional architecture. Often small molecules with three or more functional groups (f>3) conventionally used as cross-linkers can lead to increased toxicity upon degradation. One way to troubleshoot is using larger molecules with active functional groups, which however in most cases can introduce a lot of hard segments difficult to be fragmented under mild conditions. In this context, vegetable oil based polyurethanes, in particular, using castor oil in the polymeric architecture holds promise for future. Castor oil is a vegetable triglyceride with major constituent as ricinoleic acid, a trihydroxyl containing fatty acid (See, Baber, T. M. et al., *J Chem. Eng. Data* 2002, 47, pp. 1502-1505). Bio-availability from renewable agricultural resource, low cost, low toxicity, traditional medicinal use as laxative and antioxidant makes it an attractive starting material for biomedical polyurethanes under discussion. Long chains can potentially add to the flexibility in a network, ester groups as labile hydrolysable groups, inherent double bonds in combination provide for anti-oxidative properties while the free trihydroxyl functionality can be used as such for urethanation. Hydrophobicity of castor oil was effectively counter balanced by incorporation of exceedingly hydrophilic polyethyleneglycols as chain extenders in the framework. Although, the concept of using vegetable oils has increasingly gained footing in renewable polymer research (See, Biermann, U et al., *Angew. Chem. Int. Ed.* 2000, 39, pp. 2206-2226). Surprisingly, relatively very few studies have been reported on its biodegradability under physiological conditions and almost none on the use of such polyurethanes as tissue regeneration scaffolds (See, Yeganeh, H. et al., *Polym. Degrad. Stab.* 2007, 92, pp. 480-489).

To assess the various properties of the polymer network, biocompatibility must be studied in vitro. In vitro models based on immortalized or cancer cell lines provide us the necessary information about cell interactions with polymers. Information such as direct effect of polymer on cell adhesion, proliferation and viability can be investigated during in vitro experiments that are often performed in a single variant controlled environment as compared to in vivo. In-spite of cell lines being immortalized they often needs to overcome issues such as supply of cells, heterogeneity, ease of culture, and fast growth-rate. Studies using more than one cell types in in vitro models are more representative of in vivo native tissue as compared to the use of single cell types (See, Holy, C. E et al., *J. Biomed. Mater. Res.* 2000, 51, pp. 376-382).

Cells are known to remodel their surrounding extracellular matrix by secreting catabolic enzymes, such as MMPs. A strict balance between these MMPs and TIMP occurs in migrating cells that maintains the proteolytic microenvironment (See, Jennifer, L. W et al., *Macromol.* 1999, 32, pp. 241-244). Tan et al. *Carcinogenesis* 2009, 30, pp. 258-268, reported RGD peptide, $\alpha v\beta 3$ monoclonal antibody and inhibitors of mitogen-activated protein kinase inhibited the cysteine rich 61-induced increase of cell migration and MMP-13 up-regulation in chondrosarcoma cells suggesting migration of cells by increasing MMP-13 expression through $\alpha v\beta 3$ integrin receptor and Erk/MAPK signal transduction pathway. Also reports suggest that Erk/MAPK signalling has direct correlation with the expression of MMP-2 in MDA-MB-231 cells. Further reports suggest an activation of Akt via its phosphorylation mediates MMP-2 expression and thereby promoting cell invasion and proliferation (see, Shuvojit, Moulik J. et al., *Tumor* 2014, 2, pp. 87-98; Luciana, R. G. et al., *BMC Cancer* 2012, 12, p. 26; Peter Storz. et al., *Mol. Cell. Biol.* 2009, 29, pp. 4906-4917).

Oxidative stress plays a crucial role in the pathophysiology of tissue-degenerative diseases. An increase in the production of ROS by injured cells is observed at sights of tissue injury. In events of cell transplantation, transplanted cells are often unable to fight against free radicals at the tissue microenvironment (See, Rahman, T et al., *Adv. Biosci. Biotechnol.* 2012, 3, pp. 997-1019). Inflammation plays a crucial role in wound healing with evidences of both enzymatic and non enzymatic depletion of antioxidant defenses during the initial 7 days post-wounding (See, Rasik, A. M. et al., *Int. J Exp. Pathol.* 2000, 81, pp. 257-263). Hypoxic microenvironment at the wound site of cutaneous injury leads to an increased production of ROS and release of certain chemo-attractants by infiltration of activated inflammatory cells like leukocytes, neutrophils, monocytes, leucocytes and lymphocytes as cellular defense mechanism. (See, Steilinga, H. et al., *Exp. Cell Res.* 1999, 247, 2, pp. 484-494). Following the phase of hemostasis, acute inflammatory phase begins with recruitment of macrophages which secretes pro-inflammatory cytokines. Sustained recruitment of these inflammatory cells leads to chronic wounds (See, Wu, Y. et al., *Stem Cells* 2010, 28, pp. 905-915). Early phase of inflammation involves the recruitment of neutrophils which gets activated by pro-inflammatory cytokines such as IL-1$\beta$, TNF-$\alpha$, and IFN-$\gamma$ at the site of injury (see, Rosenberg, L. et al., *eMed. Plastic Surg.* 2006, 457, pp. 3-6). During the healing process of an injured tissue, re-epithelialization and granular tissue formation which consists of endothelial cells, macrophages and fibroblasts contributes towards tissue integrity. There are evidences of temporal and spatial change in leukocytes subsets during skin wound formation (Sabine, A. E. et al., *J. Invest. Dermatol.* 2007, 127, pp. 514-525). A decline in the number of inflammatory cells and pro-inflammatory cytokines during progress of healing state indicate an initialization of proliferative phase. Studies in murine wound models where the mice deficient with neutrophils, IFN-$\gamma$, TNFRp55 showed accelerated wound healing whereas with depletion in IL6 and TNF-$\alpha$ impaired the healing (Lin, Q. et al., *J. Immunol.* 2011, 186, pp. 3710-3717). The changing pattern of cytokines released from pro- to anti-inflammatory process initiates the proliferative and remodeling phase of wound healing (See, Newton, P. M. et al., *Inflamm.* 2004, 28, pp. 207-214).

Hence an ideal polymer host must satisfy the criteria such as (i) stability and biocompatibility; (ii) biodegradability and cellular penetration, and (iii) Must hold anti-oxidant and anti-inflammatory properties thereby cells can be protected against ROS and inflammatory cytokines at the site of the injury.

SUMMARY OF THE INVENTION

Accordingly, the present invention provides a biodegradable, stable and biocompatibleporous polymer scaffold synthesized from polyethyleneglycol-polyurethane (PEG-PU) with castor oil cross linkages in various cell lines and primary bone marrow stem cells. Use of porogens is quite popular to induce porosity in a polymer matrix utilizing a sacrificial approach post formation of a semi-interpenetrating polymer networks (semi-IPNs). Further to evaluate the molecular mechanism occurring during penetrability of polymer networks by cells but also its protective role against oxidative stress along with its suitability as cell delivery vehicle in an excisional wound splinting mouse model transplanted with BMSCs (BMSC+PEG-PU).

BRIEF DESCRIPTION OF ACCOMPANYING DRAWINGS

The accompanying drawings, which are incorporated into and constitute a part of this specifications, illustrate one or more embodiments and serve to explain the principles and implementations of the invention. The foregoing aspects together with the detailed description will be readily appreciated by the skilled artisan from the illustrative embodiments when read in conjunction with the drawings. In the drawings:

FIGS. 1A-1E Physico-chemical Characterization of polymer networks. (A) Representative mid-FTIR spectrum of individual reactants (a) Castor Oil; (b) Polyethyleneglycol; (c) 4,4'-diphenylmethane diisocyanate; reaction aliquots at time (mins) (d) 0; (e) 15; (f) 45; (g) 120; (h) 180 for the PEG-PU/PEGDME (50:50) semi-IPN matrix. (B) Scanning electron micrographs (cross-sectional view) of polymer films (i) before (ii) after soxhlet extraction. (C) DSC thermograms of the polymers (a) PEG, (b) PEGDME, (c) PEG-PU/PEGDME semi-IPNs (d) PEG-PU post-soxhlet extraction. (D) Representative TG-DTA plots (a) PEG-PU/PEGDME semi-IPN, (b) PEG-PU network post-soxhlet extraction. (E) Upper and lower panel indicates the polymer network before and after autoclaving at 121° C. and 15 Psi of pressure, respectively.

FIGS. 2A-2G Evaluation of stability, biodegradability and biocompatibility of polymer networks. (A) Polymer networks subjected to differential pH range of buffers. (B) Degradation of polymer networks by enzymes: trypsin (0.25%) and collagenase (1 mg/ml); and chemicals 20% TCA. (C) Viabilities of cell lines as well as primary cells cultured in presence or absence of polymer networks assessed by trypan blue dye exclusion assay. (D) Cytotoxicity imparted by polymer networks to cells was assessed using Sulphorhodamine B assay. (E)Cellular morphology of MDA-MB-231 cells in absence and presence of scaffolds (An edge of the polymer is seen in right panel). (F) MTT assay to evaluate the proliferation status of cells cultured in presence of polymers and control cells (MDA-MB-231, SK-HEP1, BMSC). (G) Hoechst staining of both MDA-MB-231 (Upper) and BMSC (Lower) cultured in presence or absence of polymer network.

FIGS. 3A-3E Cellular penetrability of polymer networks. Cellular penetrability of polymer networks: (A) Images depicting the H & E stained scaffold section of 20 µm size of only polymer network (left) as well as cultured with MDA-MB-231 (middle) and BMSC (right). (Arrow heads indicates stained cells present in the inner sections of polymer networks). (B) qPCR analysis of RNA isolated from cells penetrated inside the polymer network indicating significant increase in MMP-2 and MMP-13 whereas decrease in TIMP-2 expression. (C) Protein extracted from cells penetrated inside the polymer network depicted a phosphorylation of Akt and Erk indicating activation in signal transduction mechanisms for MMP-mediated cellular migration and proliferation. (D) qPCR analysis depicting reversal of MMP-2 and MMP-13 gene expression in penetrated cells when cultured in presence of inhibitors of Akt (Wortmannin) and Erk (PD98059). (E) Representative images of gelatin zymography suggesting activated MMP-2 and collagen zymography depicting activated MMP-13 (see, FIG. 3 in the reference #16) in cells penetrated inside the polymer network as compared to naïve cells (upper panel). Relative densitometry showing quantitation of activated enzymes in these cells (lower panel). (*p≤0.05 as compared to control).

FIG. 4. FIGS. 4A-4E Protective role of polymer network from oxidative stress (in vitro). Graphs depicting the rate of proliferation on cells cultured with polymers compared to control cells after the exposure to $H_2O_2$ (A) MDA-MB-231 (B) SK-HEP1 (C) BMSC. Images depicting apoptotic nuclei in MDA-MB-231 cells (D) and BMSCs (E) treated with 10 µM $H_2O_2$ (*p≤0.05 of control). The presence of polymer networks protected the cells from apoptosis.

FIGS. 5A-5E BMSCs transplantation using polymer network induces wound healing. (A) Representative images of wound healing in C57BL/6J mouse at post-surgery day 0 (upper) and 7 (lower, indicated with arrows) in control wound, vehicle control (PEG-PU), BMSC and BMSC-polymer network transplantation. (B) Hematoxylin-Eosin (upper) and Sirius red (lower) stained section of the regenerated wound tissue post-surgery day 7 in various groups. Quantitative analysis of positively stained (C) Hematoxylin-Eosin and (D) Sirius red cells on tissue sections of mice (N=5) at post-surgery day 7 using NIH Image J Software. (E) Relative mRNA expression levels of a panel of inflammatory cytokines were evaluated using qPCR analysis (N=5 mice). Significant difference with p≤0.05 as compared to Day 7 wound tissues of *control and #BMSC-transplantation.

FIGS. 6A-6F Polymer network depletes oxidative stress at wound site. (A) Representative images of DHE staining of sections to evaluate ROS levels at wound sites of various groups at post-surgery day 7. (B) Quantitative analysis of the ROS levels using NIH Image J software. Biochemical analyses of wound tissue on post-surgery day 7—(C) catalase activity in presence of its inhibitor 3-amino triazoles (3-AT) indicating specificity of reaction, (D) cytoplasmic (Cu/Zn-SOD) and mitochondrial (Mn-SOD) SOD activity and (E) GPx activity were evaluated in various groups implying anti-oxidant properties of PEG-PU (F) Relative mRNA expression levels of anti-oxidant enzyme genes were evaluated using qPCR analysis (N=5 mice). Significant difference with p≤0.05 as compared to Day 7 wound tissues of *control and #BMSC-transplantation.

Figure 7A:
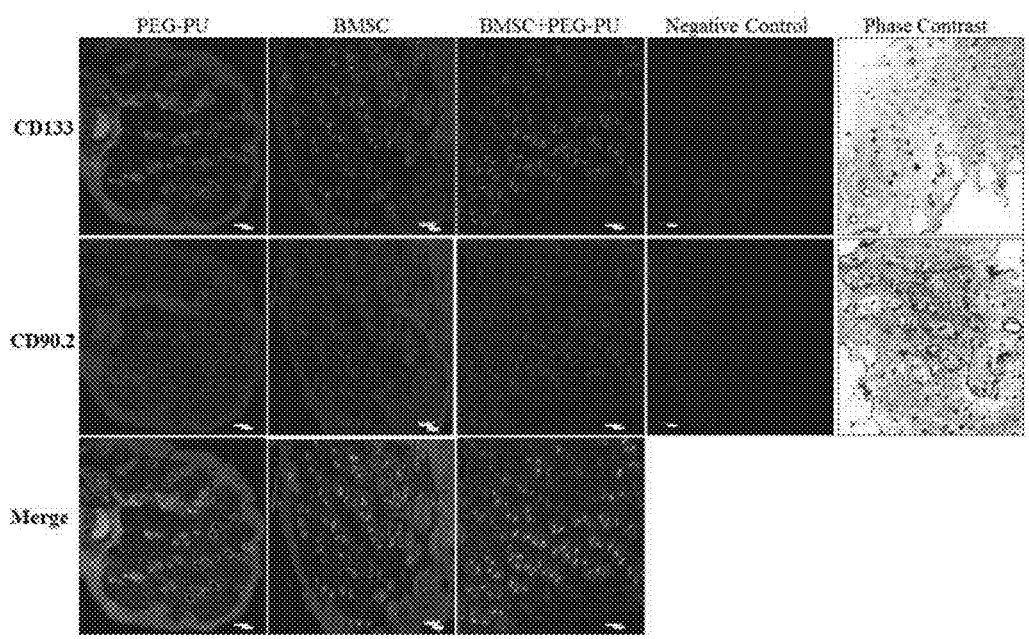
Figure 7B:
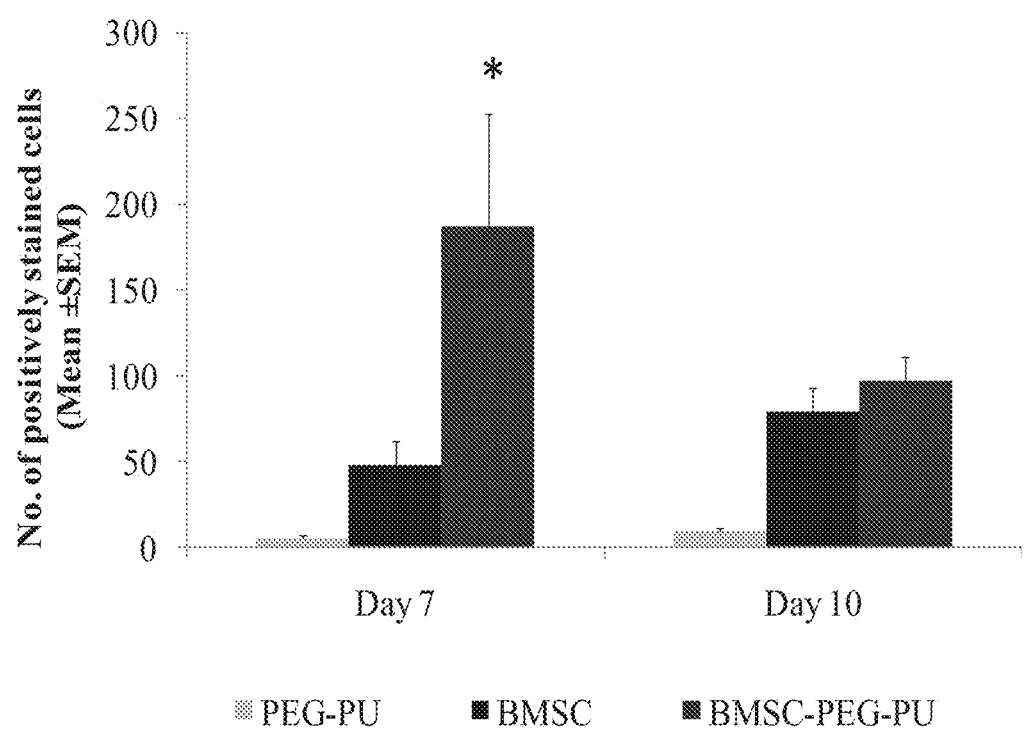

FIGS. 7A-7B Enhanced recruitment of BMSCs at wound healing site in presence of polymer network. (A) Representative confocal images of regenerated wound tissue sections stained with BMSC markers, CD133 and CD90.2 at post-surgery day 7. Sections stained with IgG-PE and IgG-APC was used as negative control. (B) Quantitative analysis of CD133 and CD90.2 positively stained cells on tissue sections of mice (N=5) at post-surgery day 7 and 10 using NIH Image J Software. Significant difference with *p≤0.05 as compared to vehicle-control (PEG-PU) wound.

Figure 8A:
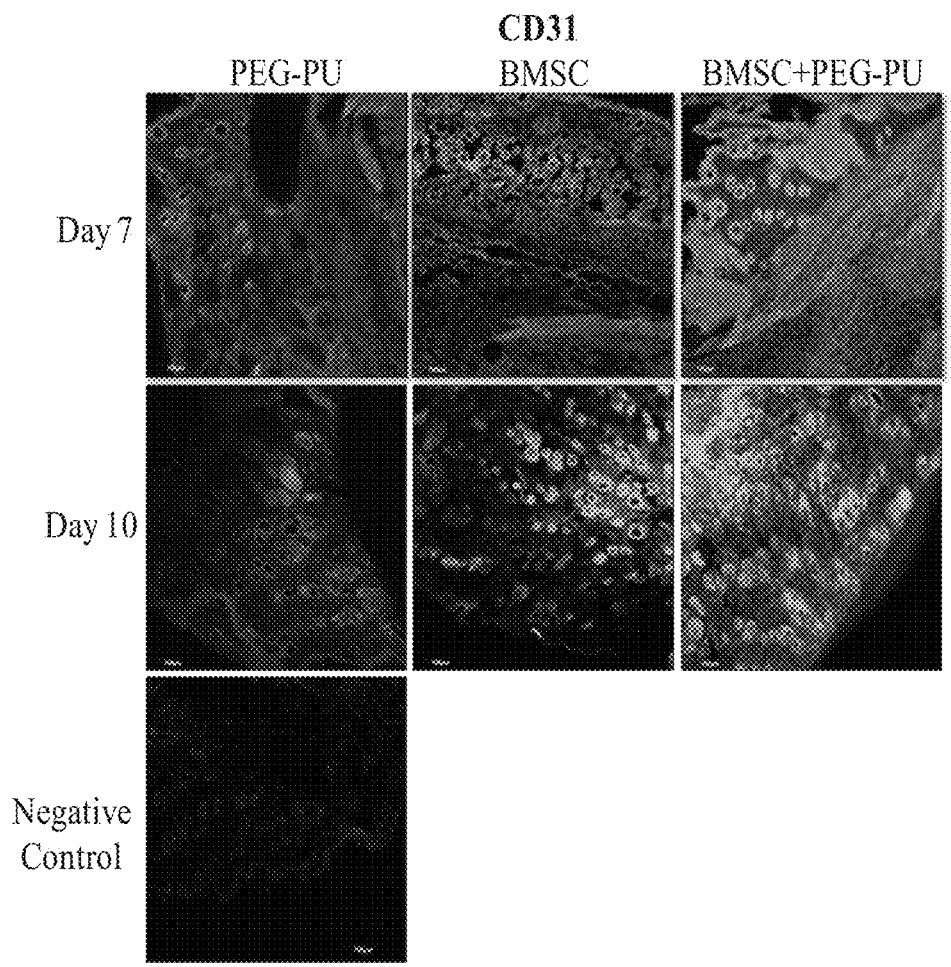
Figure 8B:
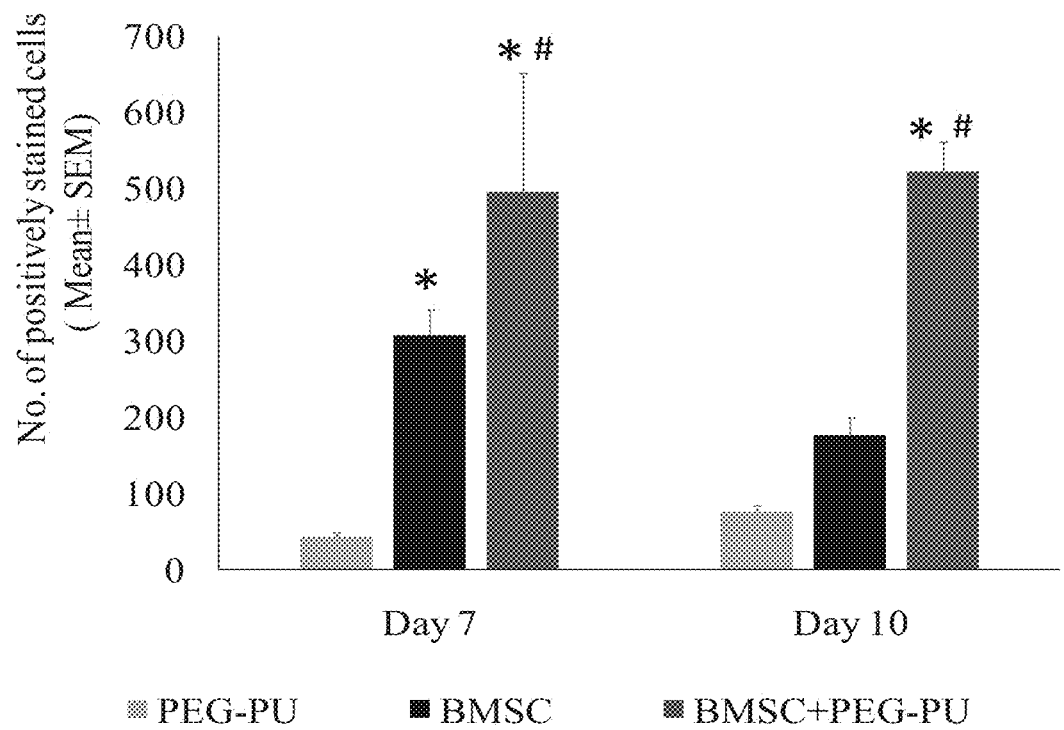
Figure 8C:
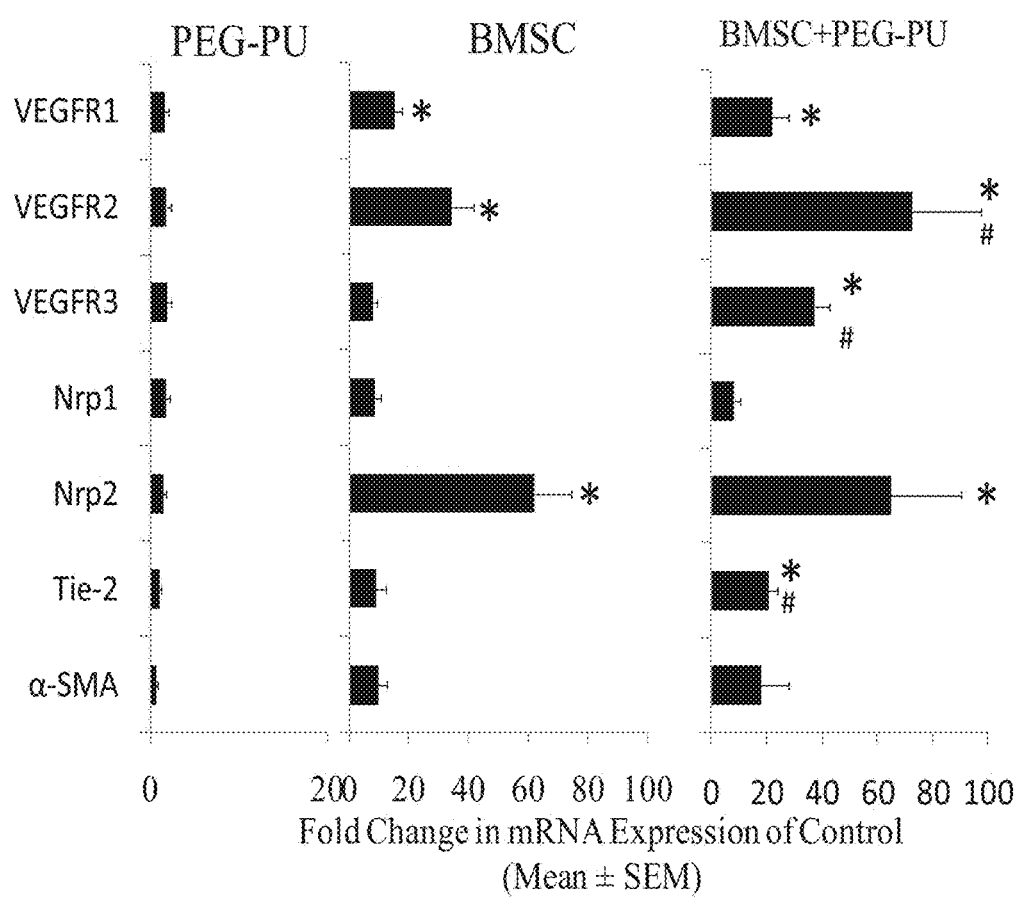

FIGS. 8A-8C Increased vascularity-mediated wound healing by BMSCs transplanted with polymer network. (A) Representative confocal images of regenerated wound tissues stained with endothelial (CD31) cell marker at post-surgery day 7 (upper) and day 10 (middle). Section stained with IgG-FITC was used as negative control (lower). (B) Quantitative analysis of CD31 positively stained cells on tissue sections of mice (N=5) at post-surgery day 7 and day 10 using NIH Image J Software. (C) Quantitative analysis using qPCR to evaluate the mRNA expression levels of various endothelial-specific receptors and neo-vascularization markers (N=5). Significant difference of p≤0.05, as compared to respective *control wound tissue and #BMSC transplanted wound tissue.

Figure 9A:
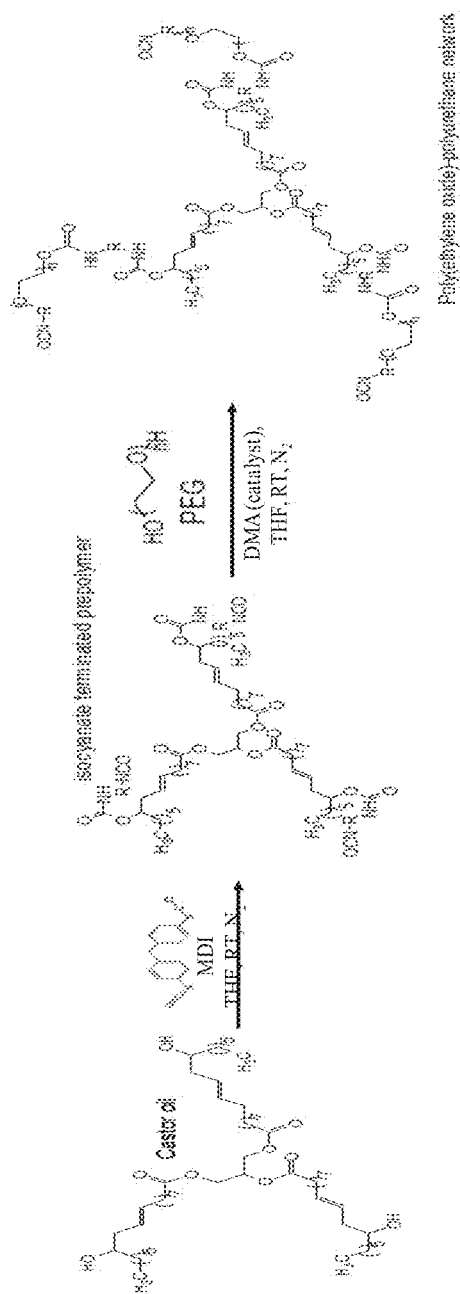
Figure 9B:
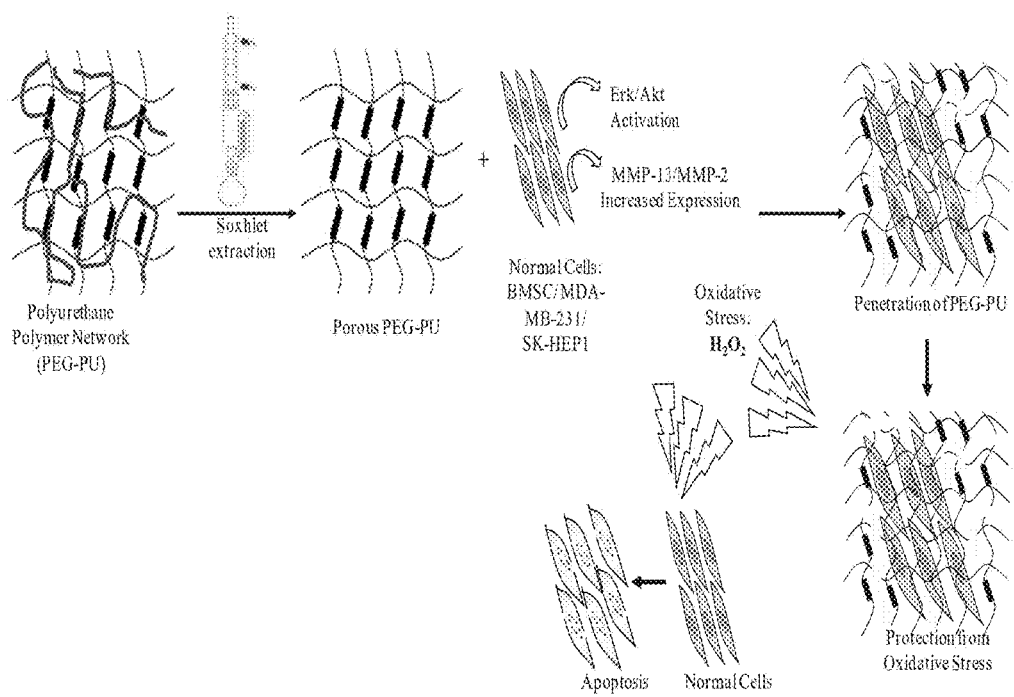
Figure 9C:
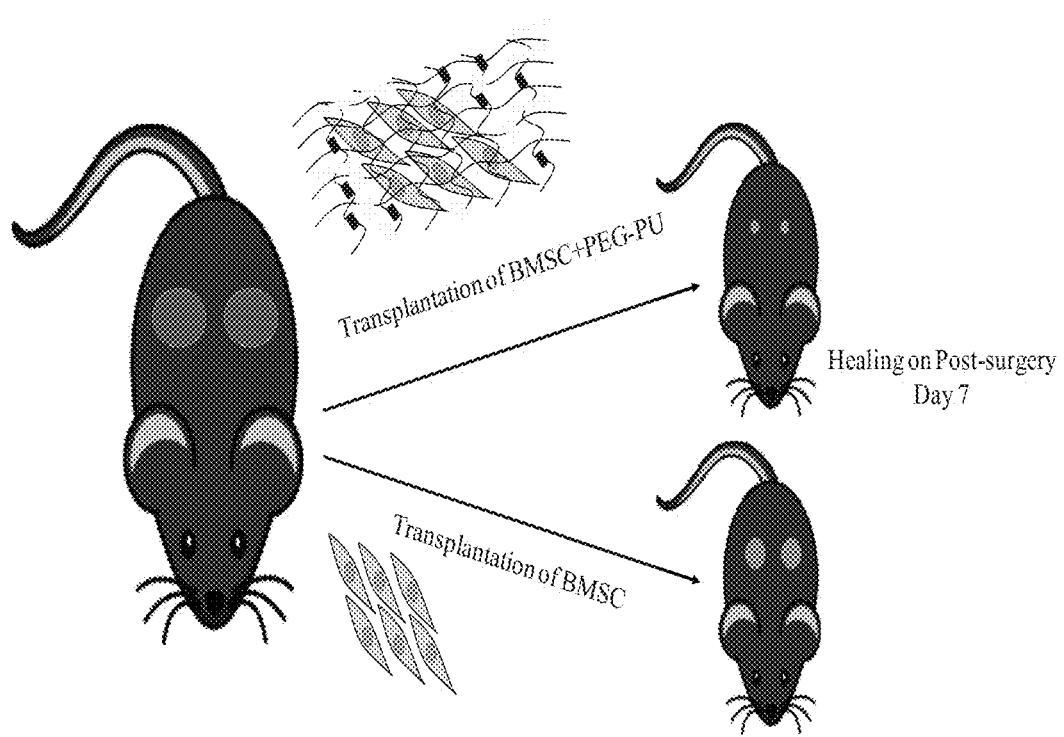

FIGS. 9A-9C Schematic representations of polymer network synthesis, cellular penetration, protection from oxidative stress and in vivo wound healing. (A) Steps involved in synthesis of polyethyleneglycol-polyurethane network (PEG-PU) from castor oil. (B) Cells when cultured in presence of polymer network undergo molecular changes such as activation of Erk and Akt signaling along with increased expression of MMP-13 and MMP-2 thereby helping it to penetrate the polymer networks. When exposed to $H_2O_2$, polymer network protects the cells from undergoing apoptosis. (C) Cartoon illustration of in vivo mouse model depicting accelerated wound healing in presence of transplanted BMSCs-polymer network.

Figure 10A:
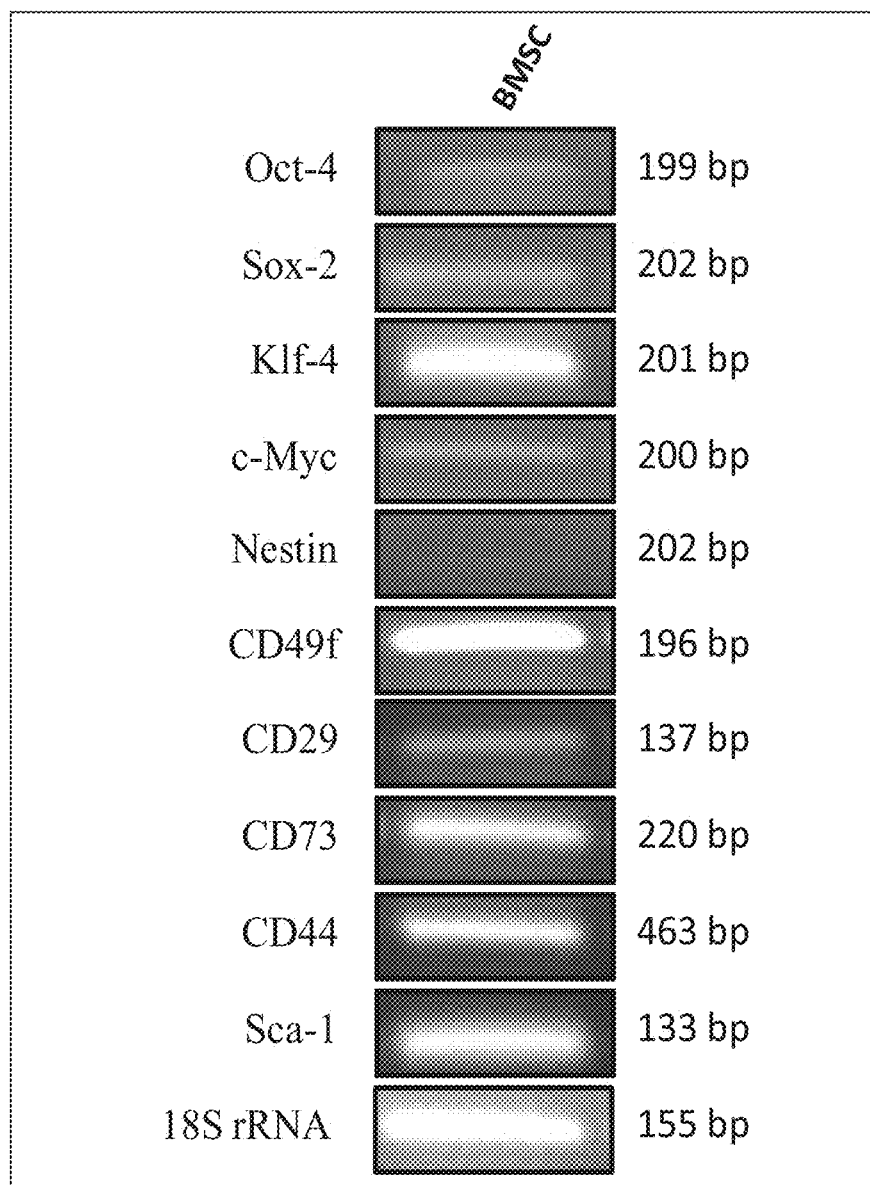
Figure 10B:
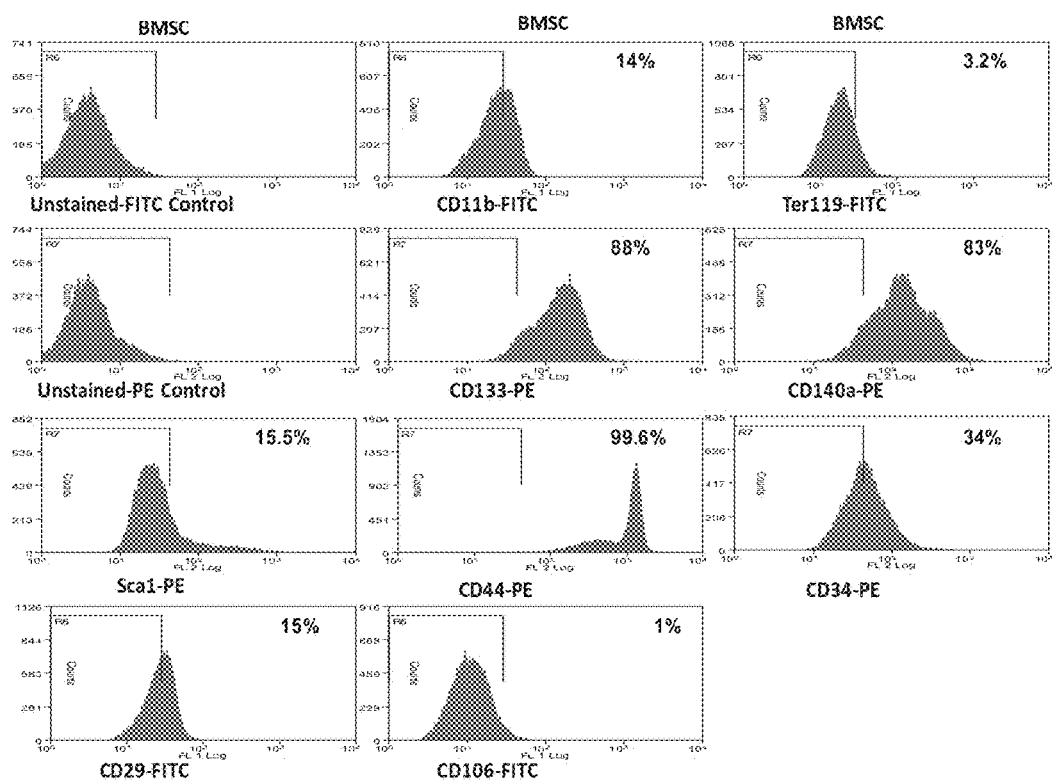

FIGS. 10A-10B Characterization of mouse BMSC. (A) Expression of mouse gene-specific mRNA of pluripotency and stem cells marker genes in the isolated BMSC cell population as analyzed using semi-quantitaitve RT-PCR depicting Oct-4, Klf-4, Sox-2 and c-Myc along with nestin, CD49f, CD29, CD73, CD44 and Sca-1. 18 S rRNAexpression has been used in the same sample as an internal control. Results shown are representative images of experiments performed more than three times. (B) Differential expression of surface proteins such as Sca-1, CD11b, CD29, CD34, CD44, Ter119, CD106, CD133 and CD140a (Biolegendlnc, USA) and Lin (MiltenyiBiotec Asia, Singapore) on BMSC as analyzed using flow cytometry. Histogram on the extreme lefts of first and second rows along with green lined in the third and fourth row represents negative control (unstained FITC- or PE-control). The data reported are representative of three independent experiments each performed in duplicates.

Figure 11:
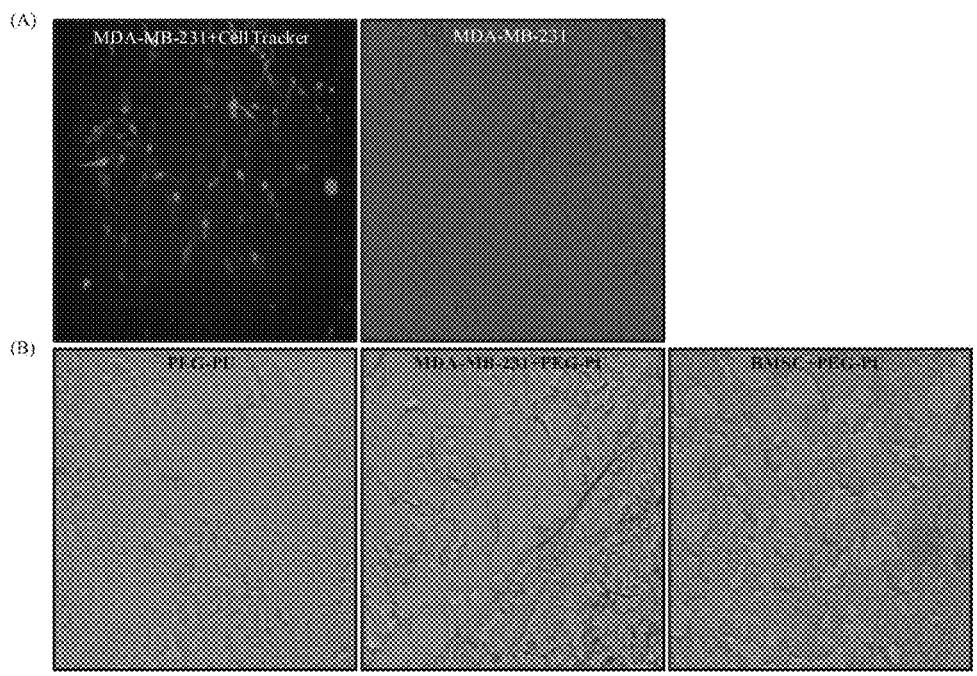

FIG. 11. Cell penetrability in polymer network. (A) Representative images of MDA-MB-231 cells labeled with cell tracker dye (left) and phase contract image (right). (B) Representative phase contrast images of polymer network cultured with or without MDA-MB-231 and BMSCs.

Figure 12:
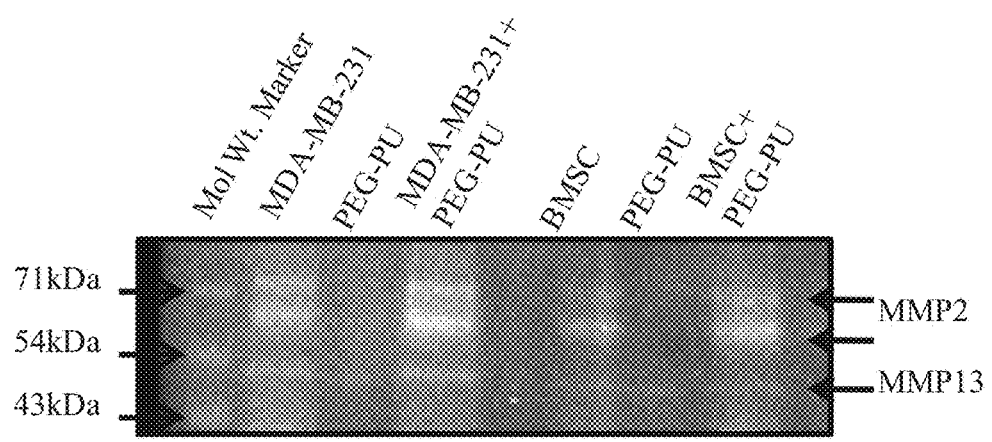

FIG. 12. Collagen zymography indicating cell penetrability in polymer network. Representative zymogram images of MDA-MB-231 and BMSCs with or without polymer network.

Figure 13:
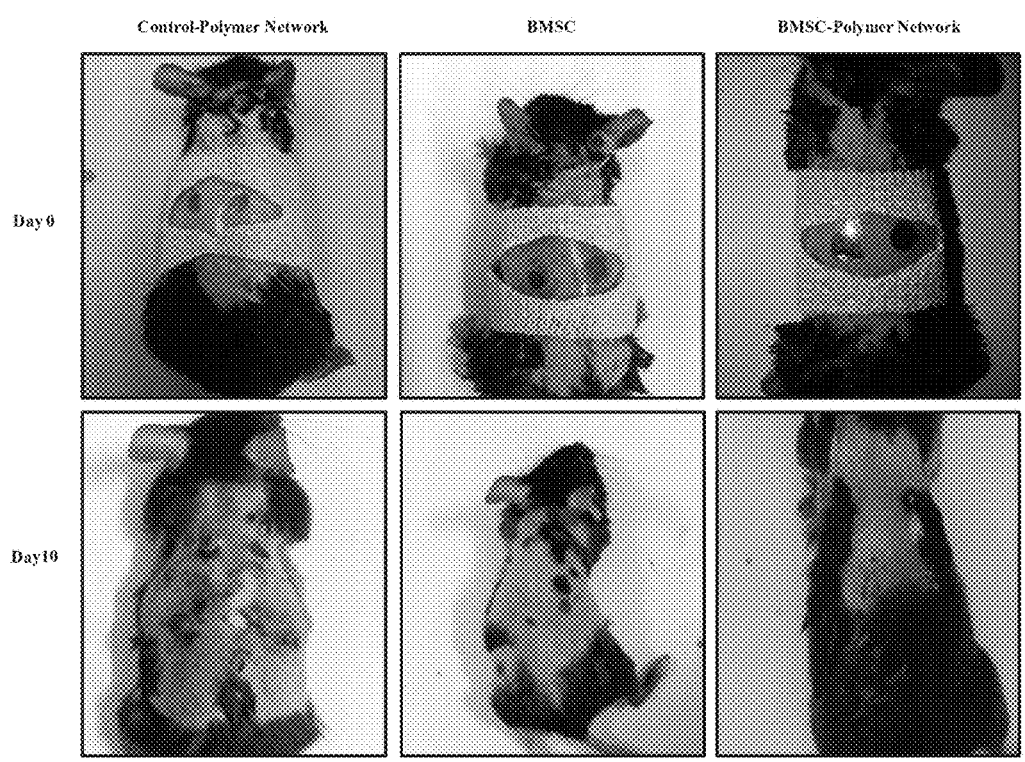

FIG. 13. Bone marrow stem cells-polymer network mediated wound healing. Representative gross images of wound tissue healing at post-surgery day 0 (upper) and day 10 (lower, indicated with arrows) in mouse with vehicle control wound (left panel) or transplanted with either BMSCs (middle panel) or BMSCs-polymer network (right panel).

Figure 14:
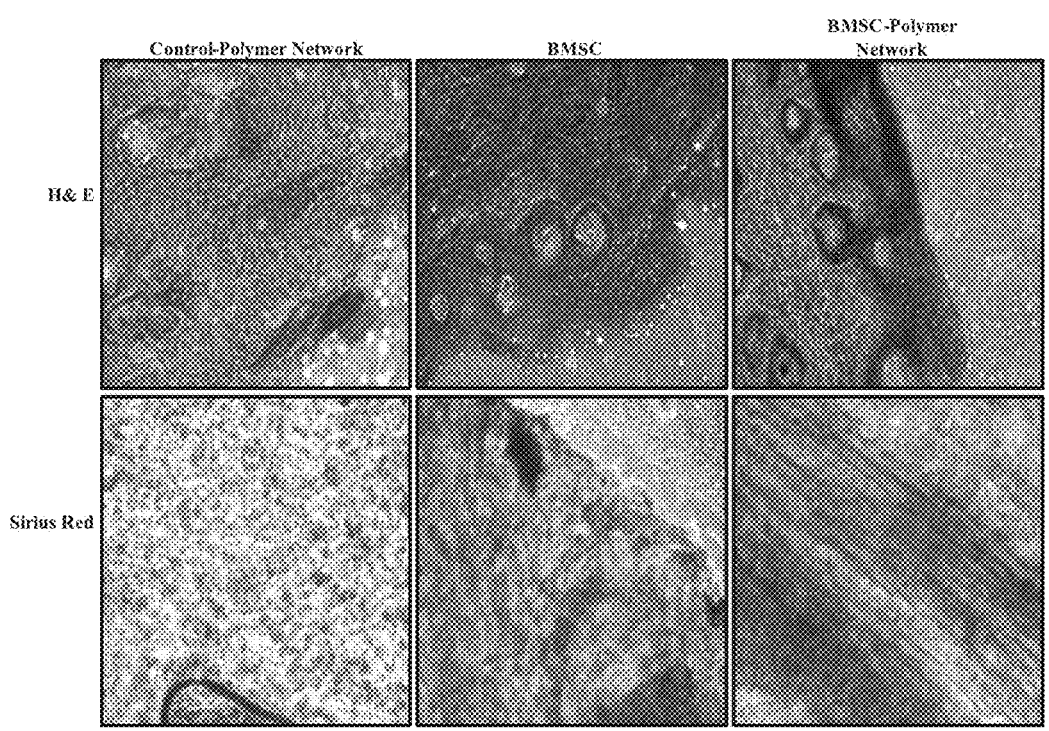

FIG. 14. Histopathological analysis of wound tissue healing in presence of BMSC-polymer network. Representative photomicrographs of Hematoxylin-Eosin (upper panel) and sirius red (lower panel) stained tissue sections from vehicle control wound (left panel) or transplanted with BMSCs (middle panel) or BMSCs-polymer network (right panel) at post-surgery day 10 (N=5).

Figure 15A:
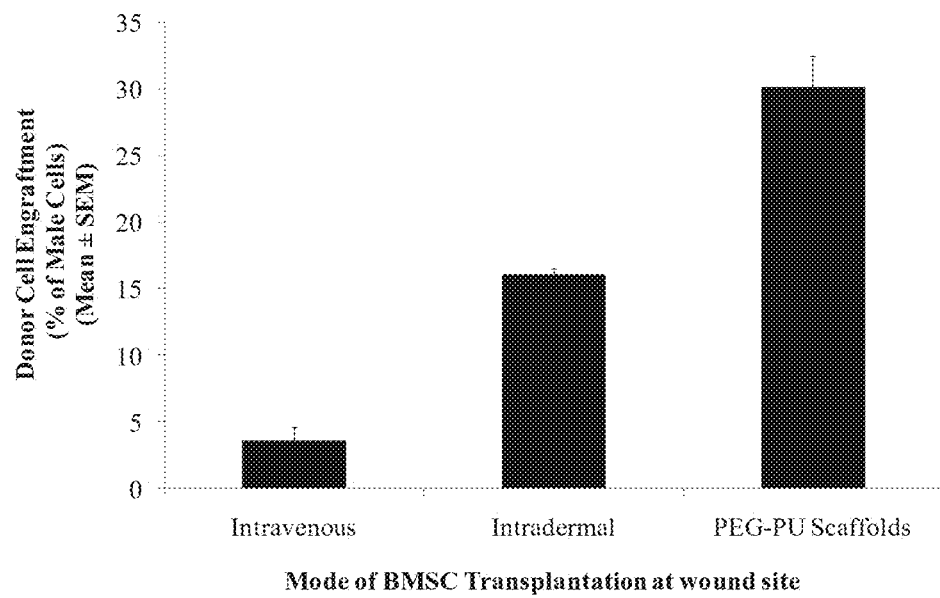
Figure 15B:
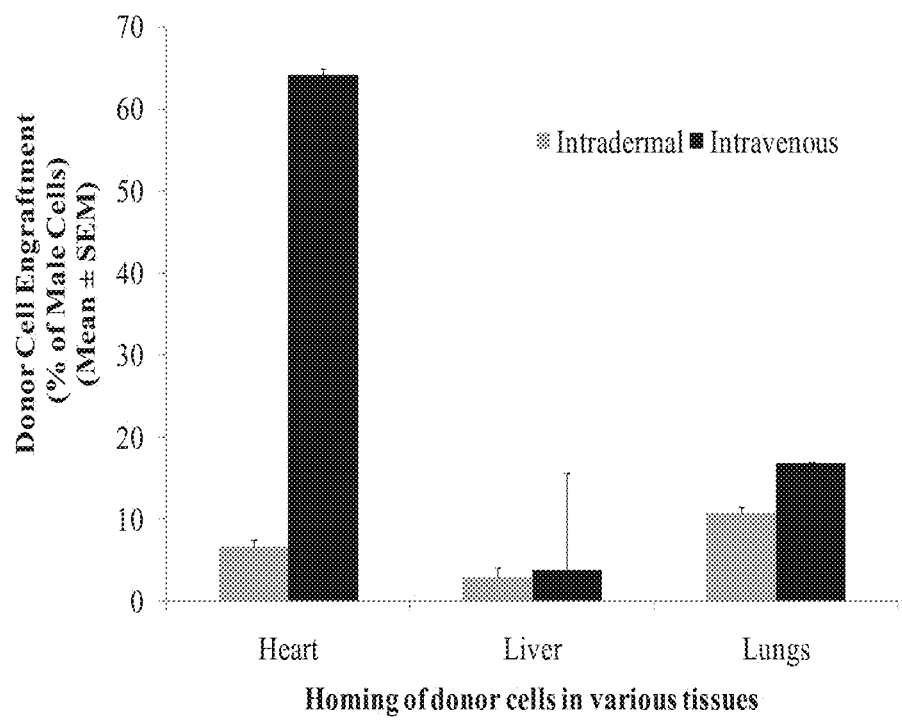

FIGS. 15A-15B BMSC homing during transplantation. BMSCs of male C57BL/6J mice were transplanted in C57BL/6J female mouse wound injury model via different sites. (A) BMSC transplantation chimeras depicting an increased engraftment of male BMSCs in female mouse wound site when transplanted locally using PEG-PU scaffolds as compared to intradermal or intravenous. (B) A large number of male BMSCs were observed to home at heart and lung tissues when transplanted intravenously.

Figure 16A:
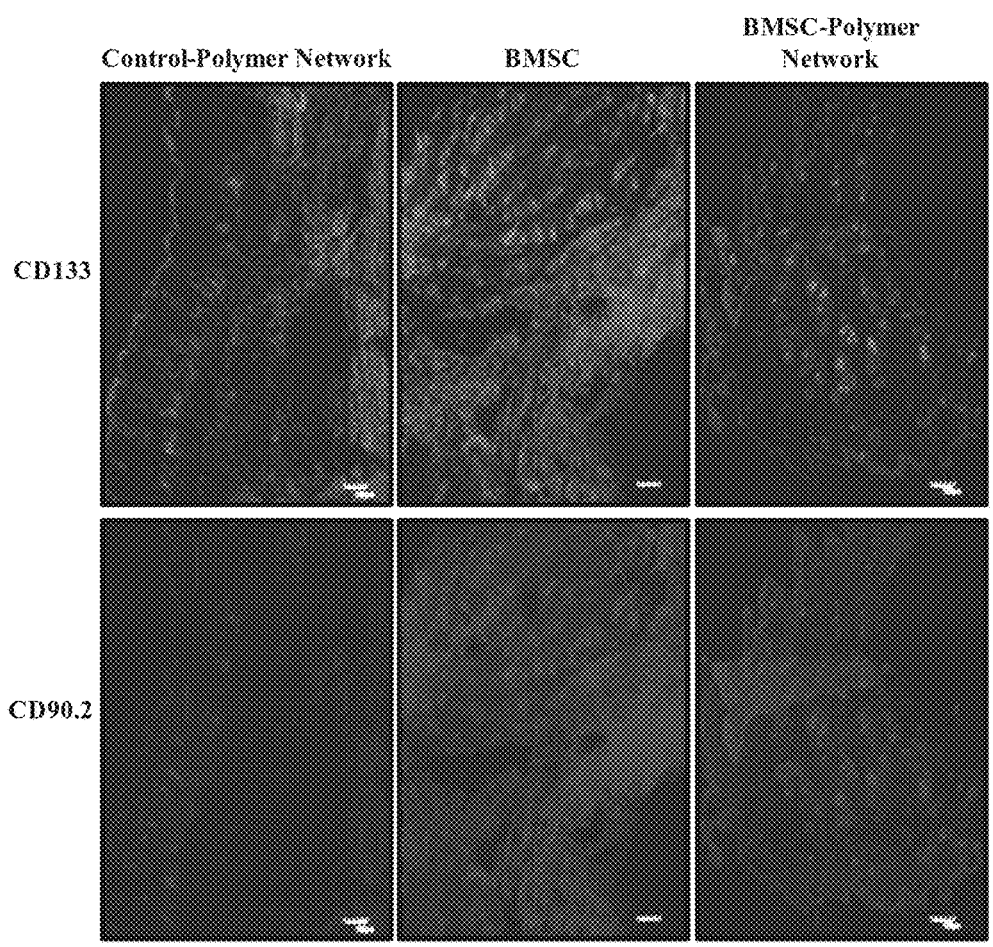
Figure 16B:
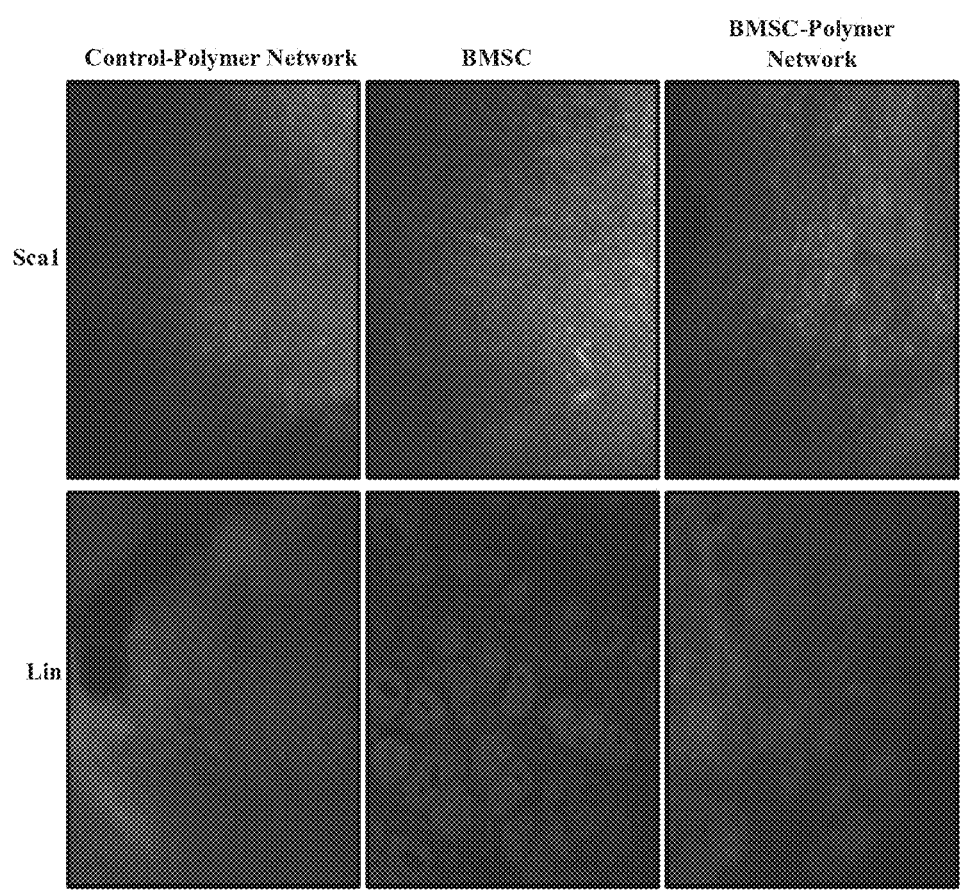

FIGS. 16A-16B BMSC engraftment at the wound site. (A) Representative confocal images of regenerated wound tissue sections stained with BMSC markers, CD133 (upper panel) and CD90.2 (lower panel) at post-surgery day 10. (B) Representative immunofluorescence microscopy images of regenerated wound tissue sections stained with BMSC positive marker, Sca-1 (upper panel) and negative marker, Lin (lower panel) at post-surgery day 10.

DETAILED DESCRIPTION OF THE INVENTION

Reference will now be made in detail to specific embodiments of the invention.

An embodiment of the present application provides a porous polymer scaffold for tissue engineering in stem cell transplantation consisting of a crosslinker, polyether backbone, an isocyanate containing compound, and a secondary component.

Another embodiment of the present invention provides the porous polymer scaffold, wherein the crosslinker is a triglyceride selected from the group consisting of castor oil, palm oil, soybean oil, cotton seed oil, and linseed oil.

Yet another embodiment of the present invention provides the porous polymer scaffold, wherein the crosslinker is a triglyceride of castor oil.

Still another embodiment of the present invention provides the porous polymer scaffold, wherein the polyether backbone is selected from the group consisting of di-hydroxyl, di-amine, and di-carboxyl terminated compounds.

In another embodiment of the present invention there is provided the porous polymer scaffold, wherein the polyether backbone is selected from the group consisting of polyethylene glycol (PEG), polypropylene glycol (PPG), polytetramethylene glycol (PTMG), block copolymers thereof, branched/graft copolymers thereof, and combinations thereof.

An embodiment of the present invention provides the porous polymer scaffold, wherein the polyether backbone is polyethylene glycol (PEG) with molecular weight of 400-10000 Daltons.

Another embodiment of the present invention provides the porous polymer scaffold, wherein the isocyanate containing compound is selected from the group consisting of methylene diphenylene diisocyanate (MDI), polymeric methylene diphenylene diisocyanate (p-MDI), toluene diisocyanate (TDI), hexamethylene diisocyanate (HMDI), dicyclohexane methylene diisocyanate (H12MDI), isophoronediisocyanate (IPDI), xylene diisocyanate, hydrogenated xylene diisocyanate, and Desmodur-N.

Still another embodiment of the present invention provides the porous polymer scaffold, wherein the secondary component is polyethylene glycol dimethylether of average molecular weight 250, 500, 750, 2000 or 5000 Daltons.

Yet another embodiment of the present invention provides the porous polymer scaffold, wherein the secondary component is polyethylene glycol dimethylether of average molecular weight 500 Daltons.

Another embodiment of the present invention provides the porous polymer scaffold, wherein pore size of said scaffold ranges from 50 nm-5 μm.

An embodiment of the present invention provides a process to prepare the porous polymer scaffold, wherein the process comprises:
(a) reacting Castor oil (10 wt % to 60 wt % of total reactant weight) with diphenylmethane-4,4'-diisocyanate (with total —NCO/—OH ratio in the range of 0.8-2.5) in tetrahydrofuran (THF) as solvent for 1 hour to form a pre-polymer (stage-I);
(b) charging the pre-polymer (stage-I) as obtained in step (a) with polyether macromonomer, N, N-dimethylaniline, and additional THF to obtain charged pre-polymer;
(c) adding a catalyst to the charged pre-polymer obtained in step (b) at room temperature to initiate the formation of a polyethylene glycol-polyurethane (PEG-PU), component-I (stage-II) and to obtain a growing polymer network;
(d) adding polyethylene glycol dimethylether (PEGDME) to the growing polymer network of step (c) to obtain a reaction mixture;

(e) degassing and vigorously mixing the reaction mixture as obtained in step (d) under inert atmosphere to obtain a uniformly homogeneous viscous mix;

(f) casting the uniformly homogeneous viscous mix as obtained in step (e) onto a teflon petri-dish to obtain a polymeric product;

(g) drying the polymeric product as obtained in step (f) at room temperature for 24 h followed by curing at higher temperature and inert atmosphere at 60-90° C. for 48 h-96 h forming a semi-IPN matrix;

(h) wrapping free standing films of the semi-IPN matrix as obtained in step (g) in Whatman filter paper bag and exposing to a repeated soxhlet extraction process to obtain processed films;

(i) subjecting the processed films as obtained in step (h) to repeated swelling and drain cycles for 4-7 days against THF to extract out the PEGDME from the semi-IPN matrix completely, leaving behind a porous polymer network scaffold with impurities; and (j) continuing extraction on the porous polymer network scaffold with impurities for 2 days using deionized millipore water (18MΩ) to obtain an impurity free and sterile porous polymer scaffold.

Still another embodiment of the present invention provides the process to prepare the porous polymer scaffold, wherein the castor oil in step (a) is 40% of the total reactant weight.

Yet another embodiment of the present invention provides the process to prepare the porous polymer scaffold, wherein the —NCO/—OH ratio of diphenylmethane-4,4'-diisocyanate is in the range of 1.2 to 1.4.

Another embodiment of the present invention provides the process to prepare the porous polymer scaffold, wherein the polyether macromonomer in step (b) is polyethylene glycol (PEG).

An embodiment of the present invention provides the process to prepare the porous polymer scaffold, wherein the polyethylene glycol (PEG) in step (b) is in the range of 70 wt % to 30 wt % of total weight.

In an embodiment of the present invention there is provided the process to prepare the porous polymer scaffold, wherein the THF in steps (a) and (b) is in the range of 20 wt % to 30 wt % of solids during reaction.

Another embodiment of the present invention provides the process to prepare the porous polymer scaffold, wherein the N, N-dimethylaniline in step (b) is in the range of 0.1 wt % to 2 wt % of solid content.

In yet another embodiment of the present invention there is provided the process to prepare the porous polymer scaffold, wherein the catalyst in step (c) is a tertiary amine.

Still another embodiment of the present invention provides the process to prepare the porous polymer scaffold, wherein the tertiary amine is dimethylaniline (DMA).

A further embodiment of the present invention provides the process to prepare the porous polymer scaffold, wherein the polyethylene glycol dimethylether (PEGDME) in step (d) has a non-reactive end group and is used in the range of 20 wt % to 70 wt % of total weight of component-I.

In another embodiment of the present invention there is provided the process to prepare the porous polymer scaffold, wherein the free standing films so obtained have an average thickness in the range of ~0.08-0.12 cm.

An embodiment of the present invention provides the process to prepare the porous polymer scaffold, wherein the polyethylene glycol dimethylether (PEGDME) is used in the weight ratio (50:50).

In another embodiment of the present invention there is provided a method of treating tissue damage and expediting wound tissue regeneration and repair, wherein the method comprises administering to a subject a composition comprising the porous polymer scaffold of the present application.

Examples of the specific embodiments are illustrated in the accompanying drawings. While the invention will be described in conjunction with these specific embodiments, it will be understood that it is not intended to limit the invention to such specific embodiments. On the contrary, it is intended to cover alternatives, modifications, and equivalents as may be included within the spirit and scope of the invention as defined by the appended claims. In the following description, numerous specific details are set forth in order to provide a thorough understanding of the present invention. The present invention may be practiced without some or all of these specific details. In other instances, well known processes have not been described in detail in order to not unnecessarily obscure the present invention.

It will, of course, be appreciated that in the development of any actual implementation of the invention, numerous implementation-specific decisions must be made in order to achieve the developer's specific goals, such as compliance with application-, performance- and business-related constraints, and that these specific goals will vary from one developer to another. Moreover, it will be appreciated that such a development effort might be complex and time-consuming, but would nevertheless be a routine undertaking of the chemistry and engineering for those of ordinary skill in the art having the benefit of this disclosure.

In the present study, we showcase the use of biodegradable porous polymer scaffolds synthesized from polyethyleneglycol-polyurethane (PEG-PU) under controlled conditions as cell delivery vehicles, tested for their stability and biocompatibility in various cell lines and primary bone marrow stem cells. As such, use of porogens is quite popular to induce porosity in a polymer matrix, however, in this study it has been achieved using a sacrificial approach post formation of a semi-interpenetrating polymer networks (semi-IPNs). Detailed studies on these scaffolds depict not only the molecular mechanism occurring during penetrability of polymer networks by cells but also its protective role against oxidative stress. Further, these polymer networks were evaluated for its suitability as cell delivery vehicle in an excisional wound splinting mouse model transplanted with BMSCs (BMSC+PEG-PU).

The successful formation of semi-IPNs are usually followed using mid-FTIR and is now well established (See, Basak, P. et al., *Eur. Polymer J.* 2004, 40, pp. 1155-1162). The sharp carbonyl peak at ~1746 $cm^{-1}$ is indicative of castor oil ester linkage, C—O—C stretching at ~1110 $cm^{-1}$ along with strong —OH stretching and bending modes at 3600-3200 $cm^{-1}$ and ca. 1630 $cm^{-1}$, are all distinctive vibrational modes of the macromonomer (polyethyleneglycol), and characteristic —NCO stretching peak of reactant N,N'-diphenylmethanediisocyanate appears at ca. 2277 $cm^{-1}$ (FIG. 1A (a-c).

During network formation via classic urethanation reaction, two significant changes are observed in aliquots withdrawn from reaction mixture as a function of time. A gradual decrease of isocyanate contribution resulted with final disappearance of the signature peak (~2277 $cm^{-1}$), indicating progress and completion of reaction (FIG. 1A d-h). Concurrently, an initial broadening followed by gradual appearance of a peak at ~1725 $cm^{-1}$ which overlapped as a shoulder to the 1746 $cm^{-1}$ peak of castor oil ester carbonyl confirms urethane formation, that finally almost merges into one broad band. Other major peaks in the spectra at ca. 3400(b), 1520(s), 2926, and 2859 cm$^{-1}$ are attributed to free N—H stretching and bending vibrational modes of urethane linkages, C—H stretching of methylene and methyl groups, respectively (See, Basak, P et al., *J. Phys. Chem. B* 2005, 109, pp. 1174-1182; Basak, P. et al., *J. Macromol. Sci-Pure Appl. Chem.* 2006, A43, pp. 369-382).

Figure 1B:
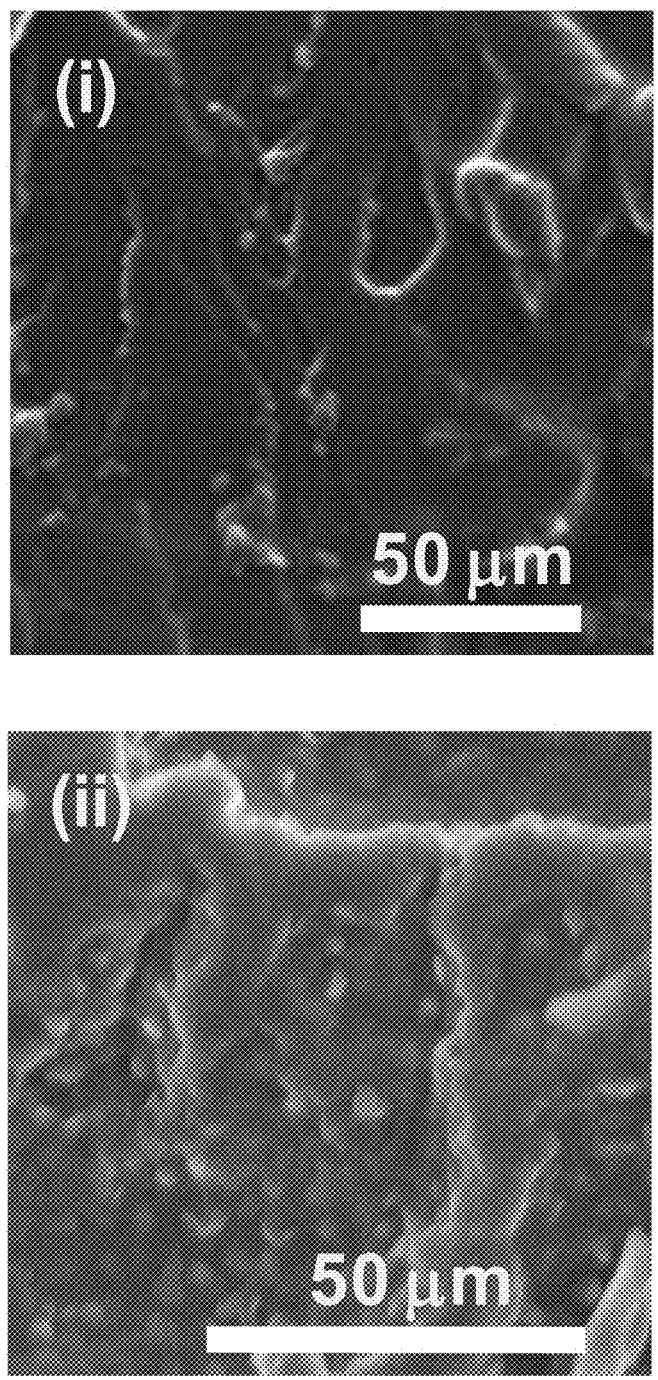

The semi-IPN morphology, matrix homogeneity, extent of phase separation and bulk porosity of synthesized films pre- and post-soxhlet extraction were probed using scanning electron microscopy. Representative electron micrographs depicting cross-sectional views of the fractured polymer films are shown in FIG. 1B. FIG. 1B-i revealed a fairly homogeneous bulk with no apparent phase separation and considerable porosity in the semi-IPN matrix. Average pore sizes of ca. 1-2 μm was observed almost evenly distributed throughout the bulk. However, post-soxhlet extraction of these films revealed a very different morphology and texture. Loss of PEGDME from the matrix and its reminiscent effects are quite evident (FIG. 1B-ii). Larger cavities with increased roughness suggest successful realization of a porous polymer scaffold as targeted in this study.

Figure 1C:
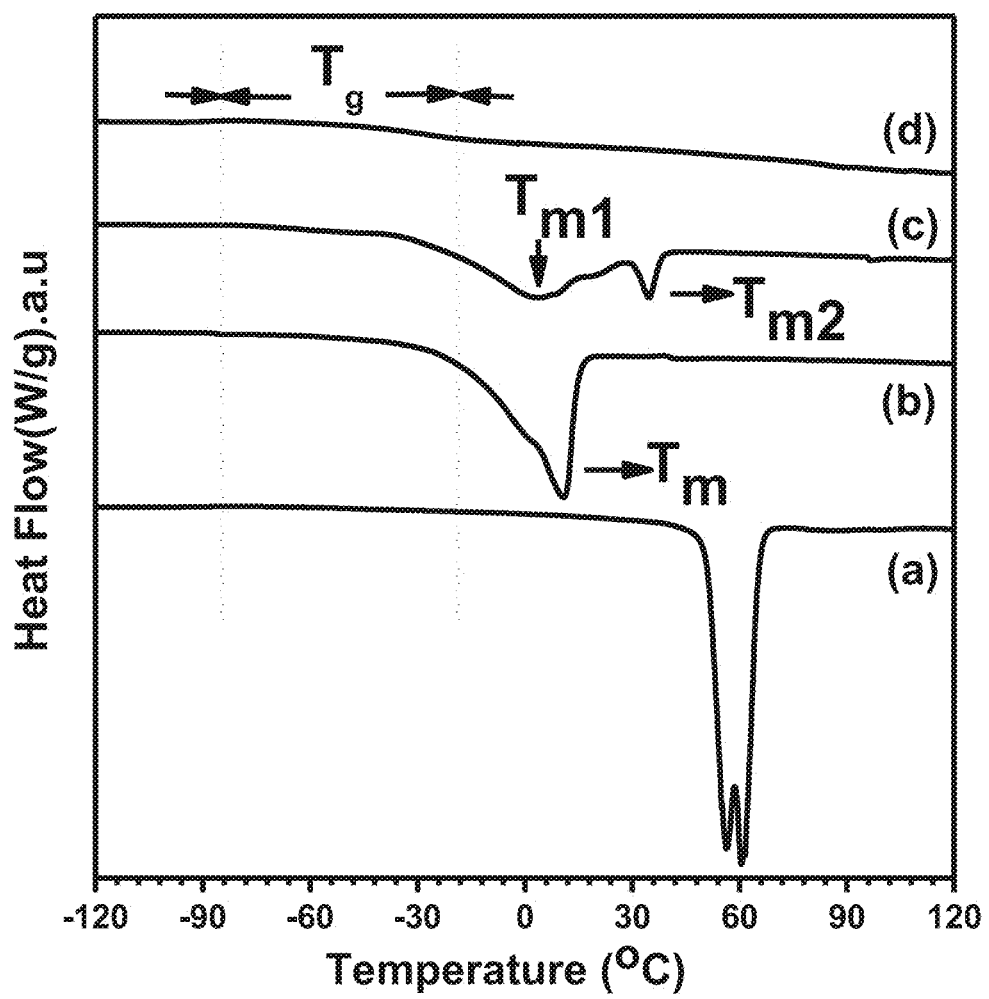

Thermal properties of polymers are important physical parameters that provide valuable insights into the overall behavior such as, miscibility, phase separation, segmental mobility, degree of crystallinity, thermal stability and degradation onset of synthesized matrices. Initial DSC studies revealed that the macromonomer, PEG ($M_n$~4000) used for network synthesis and the component-II (PEGDME), both possess a very high degree of crystallinity as evident from the thermograms. A sharp endothermic melting peak ($T_m$) at ~58° C. for PEG with an enthalpy of ca. 192 Jg$^{-1}$ corresponded to a predominantly crystalline bulk, with degree of crystallinity, % χ~94 (FIG. 1C-a). The glass transition temperature ($T_g$) could not be ascertained owing to such a high degree of crystallinity. For the oligomer, PEGDME ($M_n$=500) (FIG. 1C-b), $T_g$ was observed at ~−86° C. along with a noticeably broad $T_m$ at ~11° C. and % χ~52, contributed by the significant amount of crystalline phase present. The broad endothermic peak ($T_m$) witnessed with a prominent shoulder was due to polydispersity present in this low molecular weight oligomer. The glass transition temperature of the (50:50) semi-IPN matrix, ca. -71° C. depicts a plasticized networked matrix. The Flory-Huggins interaction parameter i.e. miscibility of the components, PEG and PEGDME are similar and hence enhanced homogeneity of the synthesized matrix was expected. Consequently, a broad glass transition temperature with an inward shift signifying good miscibility of the two polymer components used was observed. Nevertheless, clear evidence for the presence of crystallized domains was indicated with the appearance of two endothermic peaks as indicated by $T_{m1}$ and $T_{m2}$. The broad lower melting temperature peak observed, $T_{m1}$~at 3° C. was owing to the polydispersed oligomer PEGDME forming intra-molecular H-bonds. This observation suggests the existence of a small amount of exclusive crystalline PEGDME rich domains (microscopic phase separation) within the constrained confinements of the PEG-PU network. The appearance of the second endothermic peak ($T_{m2}$ at ~35° C.) was significantly shifted to lower temperature as compared to ~58° C. for the pure PEG macromonomer. This was attributed to a mixed interface formed by entangled PEG of PEG-PU network and PEGDME chains that facilitates inter-molecular H-bonding. The $T_g$ of porous polymer scaffold was observed at ~-52° C., with clear indication of a completely amorphous polymer matrix in the absence of any melting region. This observation unambiguously indicates: (i) loss of inter-chain H-bonding owing to the absence of entangled PEGDME, (ii) PEG macromonomer are randomly entangled within the crosslinked network, which in turn restricts formation of any intra-molecular H-bonding between the chains and hence cannot crystallize. The concurrent increase in glass transition temperature for the porous scaffold also suggests the loss of plasticization effect offered by PEGDME.

Figure 1D:
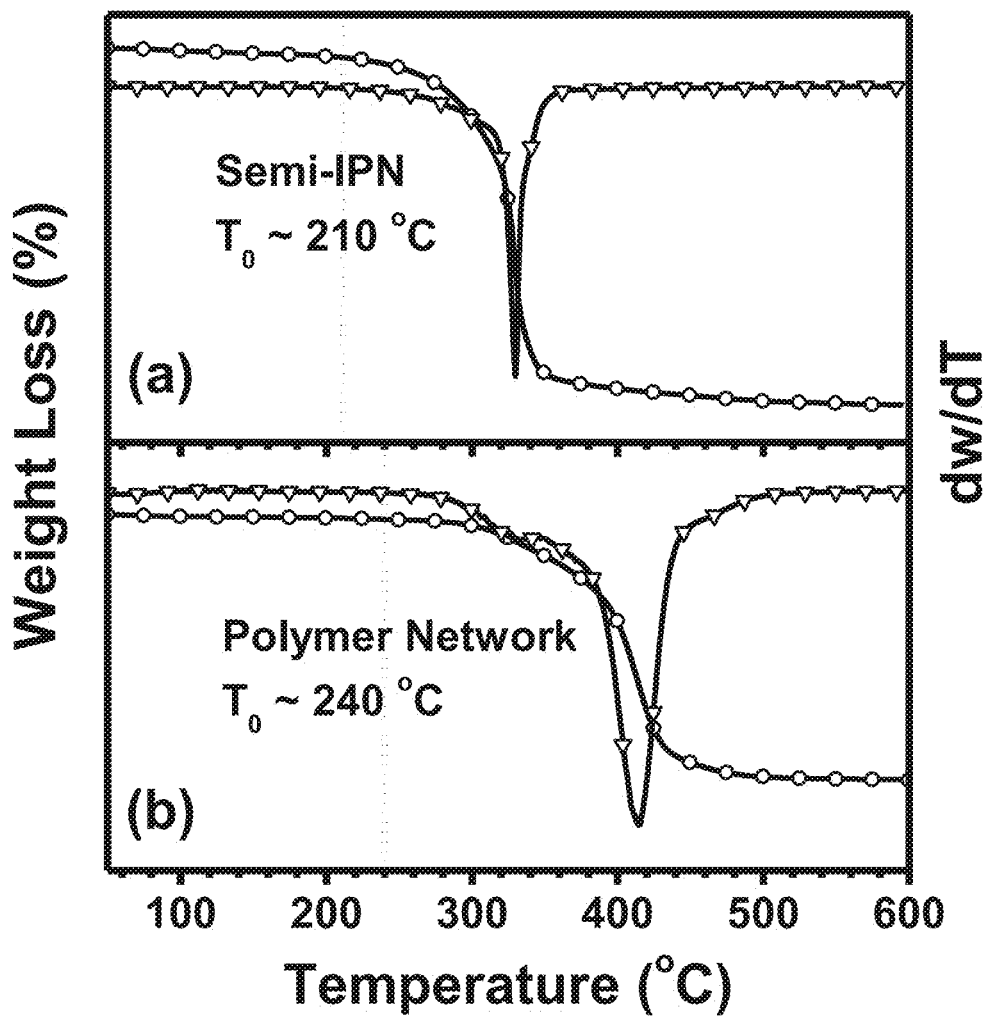

The thermal stability of the synthesized semi-IPN and porous PEG-PU network was further assessed employing thermogravimetry. An initial weight loss of ~1-3% was observed for both semi-IPNs and porous polymer scaffolds upto 150° C., possibly due to the loss of low molecular weight species, such as, absorbed moisture (FIG. 1D-a). The differential plots clearly indicate a degradation onset temperature ($T_0$) at and above ~210° C. and ~240° C. for the semi-IPN and polymer network, respectively (FIG. 1D-a). Interestingly, the higher degradation onset for polymer networks devoid of component-II can definitely be attributed to the absence of low molecular weight PEGDME. $T_0$ was followed by two stages of rapid weight loss within the temperature window of our study, as depicted in the FIG. 1D-b. The first stage, $T_{d1}$ upto ~340° C. was primarily assigned to cleavage and thermal destruction of ester bonds of castor oil. In the second stage, $T_{d2}$ (~320° C.-440° C.), weight loss occurs presumably due to cleavage of urethane linkages of polymer network.[11] The third stage of degradation beyond 450° C., $T_{d3}$, was most likely due to advanced fragmentation of chain segments formed in the first and second stage of degradation. Encouragingly, the degradation onset indicates that polymers are appreciably stable, which is an important parameter to consider for their safe usage, handling and autoclaving.

Synthesis of Semi-Interpenetrating Polymer Networks (Semi-IPN)

The process of preparing a typical semi-IPN matrix used in this study involves, reacting castor oil (BSS Grade, —OH value ~2.7, MW=932, 1.6 g, i.e. 1.7×10$^{-3}$ moles) with diphenylmethane-4,4'-diisocyanate (MDI, Merck, MW=250, 0.87 g, i.e. 3.48×10$^{-3}$ moles) in requisite amounts for 1 h using THF (Ranbaxy, 3 mL) as the solvent and nitrogen as inert atmosphere, forming a isocyanate terminated pre-polymer (stage-I). At the end of 1 h, this was charged with the polyether macromonomer (Merck, PEG, $M_n$~4000, 2.4 g, i.e. 0.6×10$^{-3}$ moles) in THF (12 mL) and N, N-dimethylaniline (DMA, Aldrich, 250 μL), room temperature catalyst to initiate the formation of a polyethylene glycol-polyurethane (PEG-PU) polymer networks, component-I (stage-II). Concurrently, the component-II, i.e. polyethylene glycol dimethylether (PEGDME, Aldrich, $M_n$~500, 4.87 g, i.e. 9.74×10$^{-3}$ moles) having non-reactive end group in the preferred weight % (50:50) was added within the system to intimately entangle at the growing polymer network. The reaction mixture was degassed and mixed vigorously for 30 minutes under inert atmosphere to obtain a uniformly homogeneous viscous mix of the desired composition. Finally, the viscous polymer solution was casted onto a teflon petri-dish, dried at room temperature for 24 h followed by curing at higher temperature and inert atmosphere to ensure the completion of isocyanate reaction (at 80° C. for 48 h) forming a semi-IPN matrix. The free standing films so obtained have an average thickness in the range of ~0.08-0.12 cm. The semi-IPN samples used in the present study were synthesized with an equal composition of component-I and component-II (50:50; respective weight percentage). The —NCO/—OH ratio was maintained at 1.1 for the urethane reaction.

Realizing Porous Polymer Scaffolds

The free standing films of the synthesized semi-IPN samples so obtained were wrapped in a Whatman filter paper bag and thereafter treated to a repeated soxhlet extraction process. Films were subjected to repeated swelling and drain cycles for 4-7 days against THF to extract out the PEGDME from the semi-IPN matrix completely, leaving behind a porous polymer network scaffold. The extraction was continued for another couple of days (2-3 days) using deionized millipore water (18MΩ) to ensure an impurity free and sterile polymer matrix. Finally, the swelled porous polymer scaffolds were transferred into potassium phosphate buffer to carry out a series of bio-feasibility studies to demonstrate the viability and potential of these synthesized polymers.

Physico-Chemical Characterizations

Fourier transform infrared spectroscopy was used to follow the formation of semi-IPN matrices in the mid-FTIR absorption range of 4000-400 $cm^{-1}$ employing a Bruker ALPHA-T instrument. Typically, monomer/polymer samples (~2-5 mg) were grinded with KBr (~200 mg) and pressed into transparent pellets of approximate dimensions, Ø=1.2 cm and t=0.02 cm; followed by vacuum drying at 60° C. for 30 min prior to each run. The transmittance spectra collected for 256 scans with a resolution interval 2 $cm^{-1}$, were corrected for baseline, atmospheric interference and also normalized when required before comparative evaluation. The polymer morphology was analyzed with scanning electron microscopy on a JEOL JSM-5600N. The cross-sections of the fractured semi-IPN matrices sputtered with gold and SEM images were acquired at different magnifications to ascertain the sample homogeneity, extent of phase separation and porosity. Differential scanning calorimetry was performed on a DSC Q200 differential scanning calorimeter (TA Instruments) under dry nitrogen atmosphere. Typically, a sample (5-10 mg) of polymer was loaded and hermetically sealed in an aluminum pan, rapidly cooled down to ~150° C. using liquid nitrogen, equilibrated for 5 min and then heated up to 150° C. at scan rate of 10° C. $min^{-1}$. The power and temperature scales were calibrated using pure indium and an empty aluminum pan was used as a reference. The analysis of thermograms was carried out using universal analysis software provided with the TA Instruments. The thermal stabilities of synthesized semi-IPNs were assessed by a TA Q500 modulated thermo gravimetric analyzer. 10 to 20 mg of semi-IPN samples were carefully weighed in an aluminum pan and TG scans were recorded at a ramp rate of 10° C./min under inert atmosphere in the temperature range 35 to 600° C.

Cell Culture

Human Breast adenocarcinoma (MDA-MB-231) cell line was maintained in RPMI 1640 (Hyclone, USA) supplemented with 10% FBS (GibcoBRL, USA). Human Liver adenocarcinoma cell line (SK-HEP1) was maintained in MEM (modified Eagle medium; Hyclone, USA) with 10% FBS. Human Breast adenocarcinoma (MDA-MB-231) cell line was procured from NCCS, Pune, India whereas Human Liver adenocarcinoma (SK-HEP1) were procured from Promo cell GmbH make marketed by KrishgenBiosystems, Mumbai, India.

Procurement of C57BL/6J Mice

Commercially the C57BL/6J mice were purchased from National Institute of Nutrition (NIN), Hyderabad (Registration Number: 154/RO/c/1999/CPCSEA). These C57BL/J6 mice were later housed and bred at the BIO-SAFE IICT, CSIR-Indian Institute of Chemical Technology, Hyderabad, India.

Primary cells isolated from mouse bone marrow were maintained in α-MEM (Sigma-Aldrich, USA) with 10% FBS. All the cells were maintained in sterile incubator with supply of 5% $CO_2$ in a humidified atmosphere. Primary mouse bone marrow stem cells were isolated from tibias and femurs of 8 weeks old C57BL/J6 mice bred in the animal care facility of CSIR-IICT, Hyderabad, India. Animal experimentation protocols were approved by Institutional animal ethics committee (approval No. IICT/CB/AD/25/06/2014/13 and IICT/CB/AD/26/08/13/08).

Trypan Blue Dye Exclusion—Viability Assay

MDA-MB-231, SK-HEP1 and mouse BMSCs were plated ($5 \times 10^3$ cells/well) in a 96-well plate and cultured in presence or absence of polymer networks. Cell morphology was monitored microscopically after 24 and 48 h. Cells from different wells were trypsinized and counted for number and viability in a Neubauer counting chamber after staining with trypan blue dye, which selectively stains non-viable cells. (See, Strobber, W. et al., Curr. Prot. In Immunol. 2001, 21, pp. A.3B.1-A.3B). The results were expressed as relative cell number (compared with control samples normalized to 0%) with standard error of Mean from experiments performed thrice with three replicates.

Sulforhodamine B—Cytotoxicity Assay

MDA-MB-231, SK-HEP1 and mouse BMSC were plated ($5 \times 10^3$ cells/well) in a 96-well plate and cultured with or without polymer networks. After 24 h, the cultured cells were fixed by means of protein precipitation using 20% TCA at 4° C. for 1 h and subsequently washed for 5 times with RO water. After drying the plates for 24 h, SRB (0.05%) in 1% acetic acid solution was added to the wells and kept in dark for 30 min. Unbound SRB was removed and bound SRB was solubilized in 100 μl/well of 10 mM un-buffered tris base solution. The absorbance was read in a 96-well plate reader at 565 nm. Results indicate the cytotoxic effect of polymer networks on primary cells as well as cell lines (Vichai, V. et al., Nat. Prot. 2006, 1, pp. 1112-1116).

MTT—Proliferation Assay

Effect of polymeric networks on the proliferation of primary cells as well as cell lines was evaluated using MTT test. MTT (3-4, 5-dimethylthiazol-2-yl)-2, 5-diphenyltetrazolium bromide) test is based on the conversion of tetrazolium soluble salt into formazan which is mediated by mitochondrial NAD and NADH—dehydrogenases present in the viable cells. Briefly, the cells were seeded at a $5 \times 10^3$ cells/0.1 ml density in 96-well plates and incubated for 48 h in presence or absence of polymer networks followed by addition of MTT reagent and further incubation for 4 h in the dark. The formazan crystals formed were then dissolved using DMSO and the end product was quantified using a microplate spectrophotometer (Perkin Elmer Enspire, Germany) at a wavelength of 570 nm (Archana, S. et al., *BMC letters* 2015, 25, pp. 680-684). The percent of viable cells cultured with the polymer networks was calculated with reference to the control sample (cells cultured without the polymer considered as having a viability of 100%).

Hoechst Staining—Apoptosis Assay

BMSCs and MDA-MB-231 cells were cultured on cover slips with and without polymers in a 6-well plate as described above. The cells were fixed with 4% paraformaldehyde and incubated with Hoechst stain (2 mg/ml) for 30 min. The excess stain was washed with PBS and the cover slips were mounted on a slide for imaging under confocal and/or fluorescent microscope. (See, Shareef, M. A. et al., *Eur J. Med. Chem*, 2015, 89, pp. 128-37).

Cell Penetration of Polymer Network Assay

After culturing the cells in the presence of polymer, they were fixed using cold methanol and dried under vacuum. Separately, polymer networks without exposed to cells were also fixed similarly and used as negative controls. Scaffold of polymeric networks embedded in a liquid gelatin-sucrose solution was placed under vacuum for 30 min followed by freezing at −20° C. Cross-sections of these scaffolds were mounted on slides and dried for 2 h. After rehydration for 30 mins, sections were stained with hematoxylin for 5-15 mins and subsequently destained with 0.5% glacial acetic acid (if over stained). Sections were then incubated with eosin for 1-2 min followed by washing with 100% alcohol. The slides were washed with xylene and mounted for imaging under microscope (See, Patrick, B. et al., *Free Rad. Biol. Med.* 2012, 53, pp. 1886-1893).

RNA Isolation, cDNA Synthesis and Quantitative RT-PCR (qPCR) Analysis

MDA-MB-231 cells were cultured in presence and absence (control) of polymers for 24 h. Cells in presence of polymers were treated with p-akt inhibitor wortmannin (100 nM) and p-ERK inhibitor PD 98059 (30 µM) for 24 h. After the incubation polymers were removed from medium, washed and homogenized to obtain cell lysate. RNA was extracted from control cells as well as cells penetrated inside the polymer using Ribozol according to manufacturer's instructions. 1 µg of template RNA was utilized to synthesize cDNA using Verso cDNA synthesis kit (Thermo Scientific, USA). Further SyBR Green PCR method was used along with specific forward and reverse primers of MMP-2, MMP-7, MMP-9, MMP-13, TIMP-1, TIMP-2 in an ABI step-one plus instrument (ABI, USA). ACTB and GAPDH expressions were used in the same reactions of all samples as an internal control. (See, Das, A et al *J. Biol. Chem.*, 2006, 281, pp. 39105-39113).

Western Blot Analysis

MDA-MB-231 cells were cultured in the presence of polymer networks for 48 h. Also polymer networks were separately, incubated with only medium. The polymer networks were removed from the wells and homogenized using RIPA lysis buffer containing protease inhibitor cocktail. Protein extracted from the cells penetrated inside the polymer was subjected to SDS-PAGE electrophoresis followed by immunoblot analysis using primary antibodies against phosphorylated Akt (p-Akt), total Akt, p-ERK and total Erk (Pierce Antibodies, USA).

Exposure of $H_2O_2$

MDA-MB-231, SK-HEP1 and mouse BMSCs were plated ($5\times10^3$ cells/well) in a 96-well plate and cultured in presence or absence of polymer networks. The cells were exposed to $H_2O_2$ at an increasing concentrations of 0.1, 1 and 10 µM. MTT assay was performed as described above to evaluate the proliferative potential of cells whereas, Hoechst staining was performed to evaluate the apoptosis of cells in presence of polymer networks.

Animal Experiments

Procurement of C57BL/6J Mice:

Commercially the C57BL/6J mice were purchased from National Institute of Nutrition (NIN), Hyderabad (Registration Number: 154/RO/c/1999/CPCSEA). These C57BL/J6 mice were later housed and bred at the BIO-SAFE IICT, CSIR-Indian Institute of Chemical Technology, Hyderabad, India.

Isolation of Mouse BMSC

C57BL/J6 mice were used for the isolation of BMSC. Briefly, bone marrow from tibias and femurs of 8 weeks old C57BL/J6 mice were flushed out using αMEM. Subsequently, cells were plated using the same medium containing 10% FBS and 1% penicillin-streptomycin for 72 h with repeated changes of medium and subsequently passaged to perform experiments. (These cells were characterized using RT-PCR for pluripotency and stem cell markers Oct-4, Sox-2, Klf-4, c-Myc along with nestin, CD49f, CD29, CD73, CD44 and Sca-1 gene expressions. 18 S rRNA expressions have been used in the same sample as an internal control. Flow cytometry analysis was also performed for various surface protein markers expression such as CD133, CD44, CD29, CD34, CD106, CD140a, Sca-1, CD11b and Ter119 (FIG. 10). The above mentioned protocol was approved by the Institutional animal ethics committee (approval No. IICT/CB/AD/25/06/2014/13).

Excisional Wound Splinting Mouse Model 8-10 weeks old C57BL/6J mice were used for generation of excision wound splinting model as described earlier. (See, Wang, X et al., *Nat. Prot.* 2013, 8, pp. 302-309). Mice were anesthetized using an intraperitoneal (ip). injection of sodium pento-barbital (50 mg/kg). The hair on dorsal side was removed by applying hair removal cream followed by disinfection of skin surface with povidine-iodine solution. Two symmetrical full-thickness excisional wounds were created besides the midline using 5-mm-diameter sterile biopsy punch. Transplantation of BMSCs was performed by injecting intradermally (id.; $0.7\times10^6$ cells) and on the wound surface ($0.3\times10^6$ cells). In a separate group, BMSCs were cultured in presence of 5 mm-diameter polymer network and implanted as described above, along with placing of the polymer network on the wound surface. A similar 5 mm diameter punched silicon splint ring was adhered around the wound and stitched at the corners to prevent the wound healing due to contraction of the skin and wound was dressed with transparent bandage. The above mentioned protocol was approved by the Institutional animal ethics committee (approval No. IICT/CB/AD/26/08/13/08).

Gene Expression Studies

RNA was extracted from wound tissue samples of control, vehicle control (PEG-PU), BMSC, BMSC+PEG-PU post surgery day 7. The forward and reverse primers of inflammatory cytokines (pro-inflammatory cytokines IL1, IL2, IL3, IL5, IL6, IL8, IL 17, IL18, IFNγ, TNF-α and anti-inflammatory cytokines IL10, IL13), anti-oxidant enzymes (Catalase, SOD1, SOD2, GPx1, GPx2) along with endothelial cell markers (VEGFR1, VEGFR2, VEGFR3, Nrp1, Nrp2, Tie2, α-SMA) was used to perform quantitative PCR analysis as described earlier. (See, Lau, K-H. W. et al., *Bone* 2013, 53, pp. 369-381).

Histopathology Studies

Regenerated wound tissue samples from post-surgery day 7 and 10 of control wound, Vehicle control (PEG-PU), transplanted BMSC and BMSC-polymer network mice using 5 mm biopsy punch were fixed in 4% paraformaldehyde. The wounds were mounted on cryo-block using OCT to make sections of thickness 10 µm using cryotome (Leica).

Hematoxylin and Eosin Staining

Cross-sections of skin were mounted on slides and fixed using cold acetone for 10 min. After rehydration for 30 mins, sections were stained with hematoxylin for 5-15 mins and subsequently destained with 0.5% glacial acetic acid (if over stained) and washed. Sections were then incubated with eosin for 1-2 min followed by washing with 100% alcohol. The slides were washed with xylene and mounted for imaging under microscope.

Sirius Red Staining

The sections were stained with Sirius red for 30 min to evaluate collagen deposition at the regenerated wound site. The stained sections were washed under running tap water for 2 min. The slides were counter stained with Haemotoxylin and washed in xylene and mounted.

DHE Staining

Post-surgery day 7 samples from all the four groups; control, vehicle control, BMSC transplanted with and without polymer network wounds were embedded in 4% paraformaldehyde and sections were made with thickness of 10 μm using cryotome. The sections were stained with Dihydroethidium (DHE) (10 μM) solution for 30 min. DHE or hydroethidium is a compound which penetrates into the cells and interacts with $O_2^-$ thereby forms a byproduct known as oxyethidium. This product upon interaction with nucleic acids emits red color, qualitatively detected by confocal microscope.

Immuno-Fluorescence Analysis

The frozen sections were fixed with cold acetone and dried for 30 min. The slides were washed with PBS and incubated in normal goat serum (1:10 dilution) for 1 h. After blocking, the blocking buffer was drained and incubated with antibodies CD31-FITC, CD133-PE, and CD90.2-APC for overnight at 4° C. The slides were washed in PBST to remove unbound antibodies. Negative control slides were prepared simultaneously without primary antibodies. The slides were subsequently washed in xylene and mounted using DPX mounting medium to view under confocal microscope (Olympus FluoView. (See, Lin, Q et al., *J Immunol.* 2011, 186, pp. 3710-3717).

Image Analysis

The image files were opened using ImageJ software followed by conversion in 16-bit by various sequential steps provided in the software: Edit—Options—Scale. The staining was quantified by adjusting the threshold in the following steps: (1) "Image—Adjust—Threshold"—The auto/manual setting was used to select all the stained portions, (2) Process—to subtract background with rolling ball then—apply, (3) Process—binary—watershed, (4) using "Analyze—Set Measurements" options finally selected the parameters to be measured. To make sure that only the selected gray level measurements are quantified, "Limit to Threshold" option was used, (5) "Analyze—Measure," results appeared in a table form was saved and graphs were made by transferring this data to excel file, (6) "Analyze—Analyze Particles" has been used to measure individual feature profiles. Intensity measurements are performed within regions of interest by choosing the parameters at step 5 (Ellen C. J. et al., *J The Anatomical Records*, 2013, 296(3), pp. 378-381).

Biochemical Antioxidant Enzyme Assays

The regenerated wound tissue samples harvested on post-surgery day 7, using 5 mm biopsy punch with the same diameter of excision were homogenized in respective sample assay buffers for antioxidant enzyme analysis such as Catalase, SOD and GPx.

Catalase (CAT); The catalase activity assay was performed by the method of Aebi (1984). The homogenized sample in phosphate buffer (pH 7.2) was centrifuged at 12000 rpm for 30 min. The supernatant collected was used for analyzing catalase activity in presence of $H_2O_2$. The decrease in the absorbance measured at 240 nm represents the rate of decomposition of $H_2O_2$ by the catalase present in the sample.

Superoxide Dismutase (SOD); Both cytosolic (Cu/Zn-SOD) and mitochondrial (MnSOD) were extracted from the samples using differential centrifugation technique as suggested by the manufacturer's protocol, superoxide dismutase assay kit (Cayman chemicals, USA). In this assay, xanthine oxidase and hypoxanthine system generates the superoxide radicals. One unit of SOD defined as the amount of enzyme needed to exhibit 50% dismutation of the superoxide radical (See, Ismail, N. et al., *Saudi J. of Gastroenterology*, 2010, 16(2), pp. 90-94).

Glutathione Peroxidase (GPx); GPx activity was assayed using GPx assay kit (Cayman Chemicals, USA). This assay measures GPx activity indirectly by a coupled reaction with glutathione reductase (GR). Oxidized glutathione (GSSG) produced upon reduction of hydroperoxide by GPx, further recycled to GR and NADPH. This oxidation was measured spectrophotometrically at 340 nm (See, Ismail, N. A. et al., *Adv. In Biosci. & Biotech.* 2012, 3, pp. 972-977).

EXAMPLES

The following examples are given by way of illustration of the present invention and its use, however, it should not be construed to limit the scope of invention.

Example 1: Stability of Polymer Networks

Figure 1E:
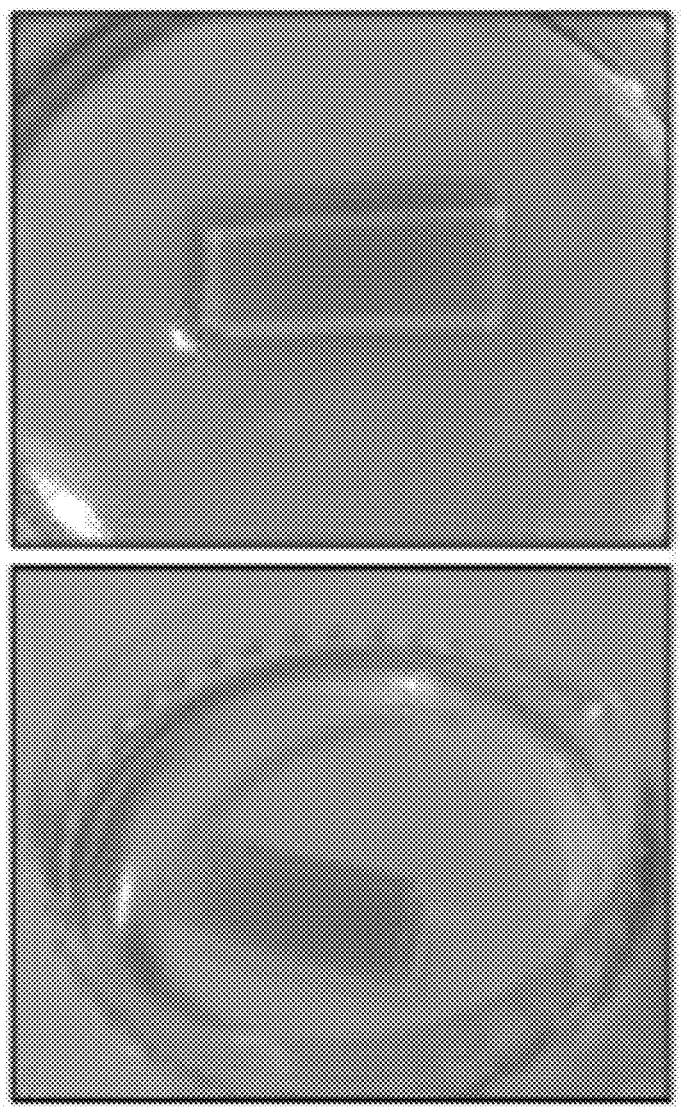
Figure 2A:
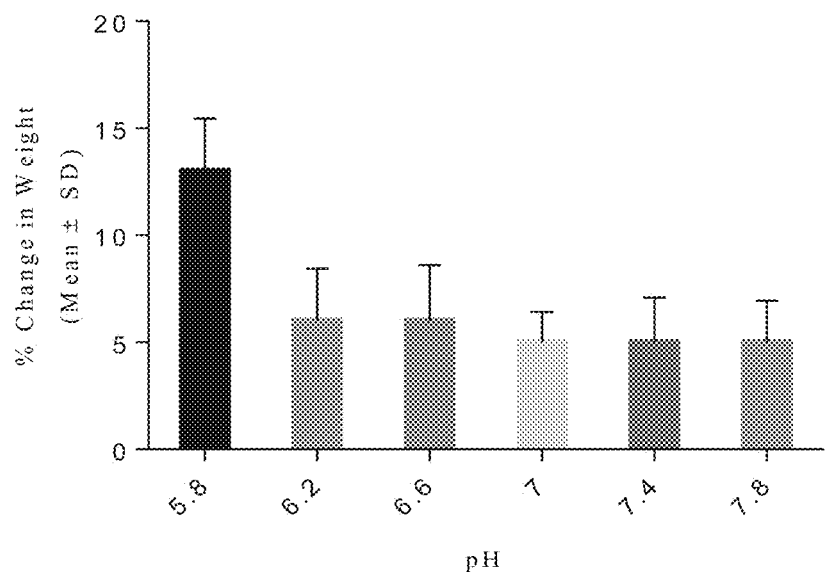

Polyethyleneglycol-polyurethane networks when subjected to autoclaving (121° C. temperature and 15 psi pressure) did not exhibit any significant changes confirming high thermo- and barostablity (FIG. 1E). Often suitability of the polymer network depends upon its biodegradability and rate of release of implanted cells to interact with in vivo microenvironment. In pathological conditions, cellular damage including injury to lysosomal membranes results in leakage of their enzymes into the cytoplasm and activation of acid hydrolases that leads to acidic intracellular pH. Thus targeting acidic microenvironment of injured tissue often necessitates the delivery vehicles with pH-sensitive degradation in order to release cells at a controlled rate. (See, Stubbs, M et al., *Mol. Med.* 2000, 6, pp. 9-15). Interestingly, when the networks were subjected to buffers of different pH, they showed an increased degradation at acidic pH 5.8 (2.5-fold percent change in weight) as compared to normal physiological pH 7.4 indicating a pH sensitive degradation profile (FIG. 2A). The half-life period observed were 3.9 days at pH 5.8 and 8.3 days at physiological pH.

Example 2: Biodegradability of Polymer Networks

Figure 2B:
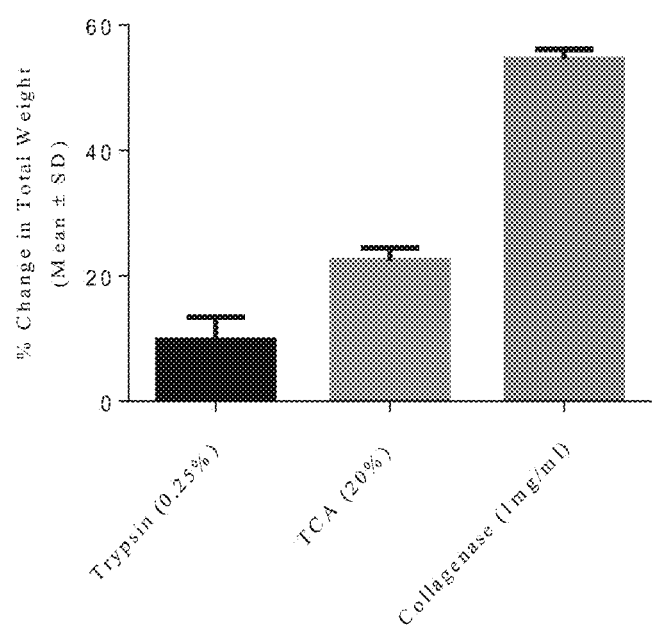

Polymer degradation in presence of biocatalysts indicates the feasibility of use as cell delivery vehicles in transplantation therapies. Bio-catalytic degradation studies performed for 24 h, revealed 50% degradation in presence of collagen at 1 mg/mL and a relatively less degradation (13%) in presence of enzyme 0.25% trypsin (FIG. 2B). Polymer networks also showed 22.3% degradation over period of 24 h in presence of 20% TCA suggesting chemical hydrolysis by the reducing agent. The results imply that these polymer networks can efficaciously release cells making them a probable cell delivery vehicle.

Example 3: Biocompatibility of Polymer Networks

Figure 2C:
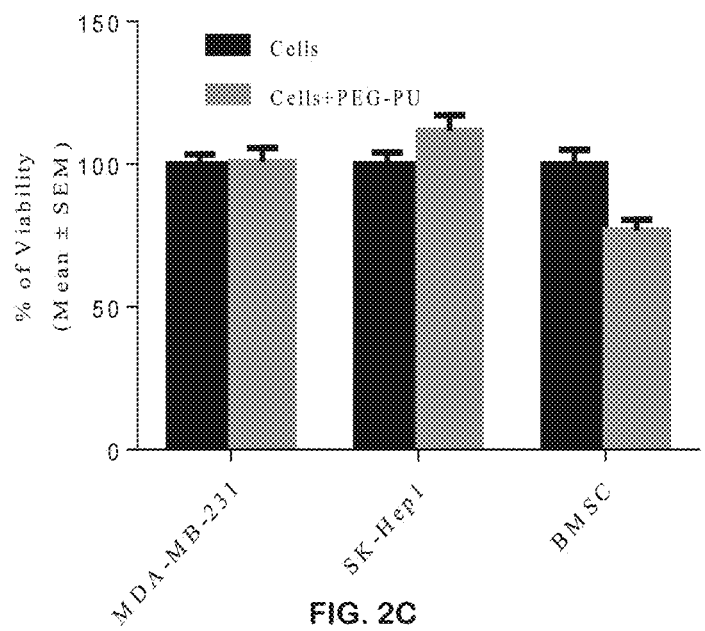
Figure 2D:
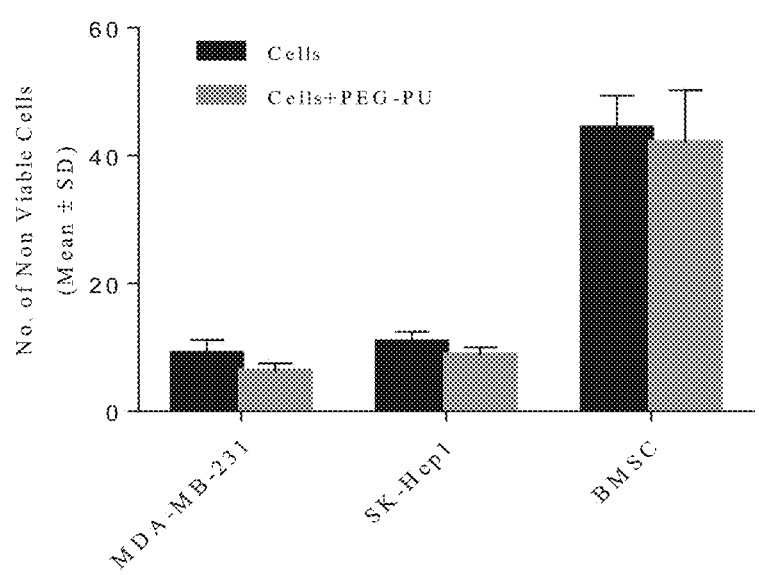

The polymer networks when tested for their cytotoxic effect on cells such as MDA-MB-231, SK-HEP1 and mouse BMSCs depicted an insignificant difference on viability in presence or absence of polymer networks. Trypan blue dye exclusion assay performed to evaluate the stained dead cell population also revealed no significant difference between cells cultured with or without polymer networks (FIG. 2C). Furthermore, SRB Assay performed to evaluate the cytotoxicity imparted to the cultured cells showed an insignificant difference between results of cells cultured in absence or presence of polymer networks (FIG. 2D).

Example 4: Analysis of Cellular—Morphology and Proliferation

Figure 2E:
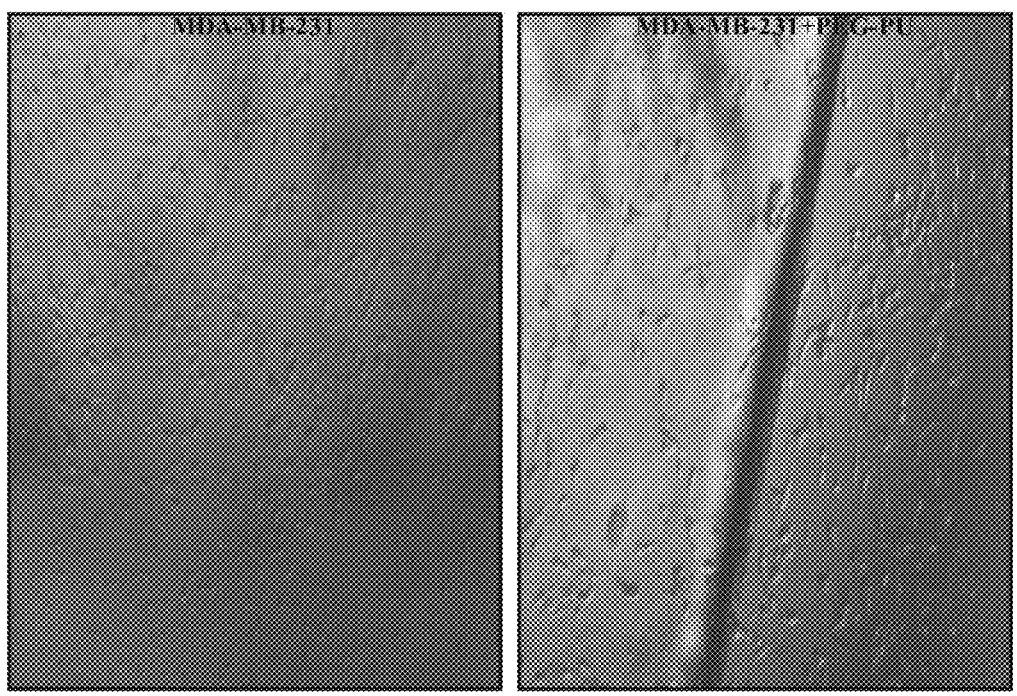
Figure 2F:
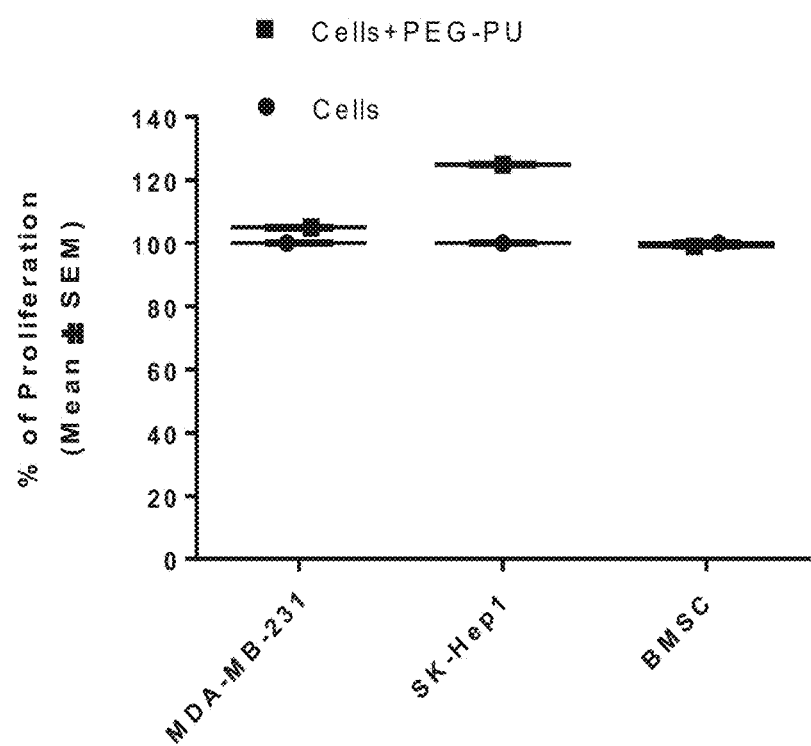
Figure 2G:
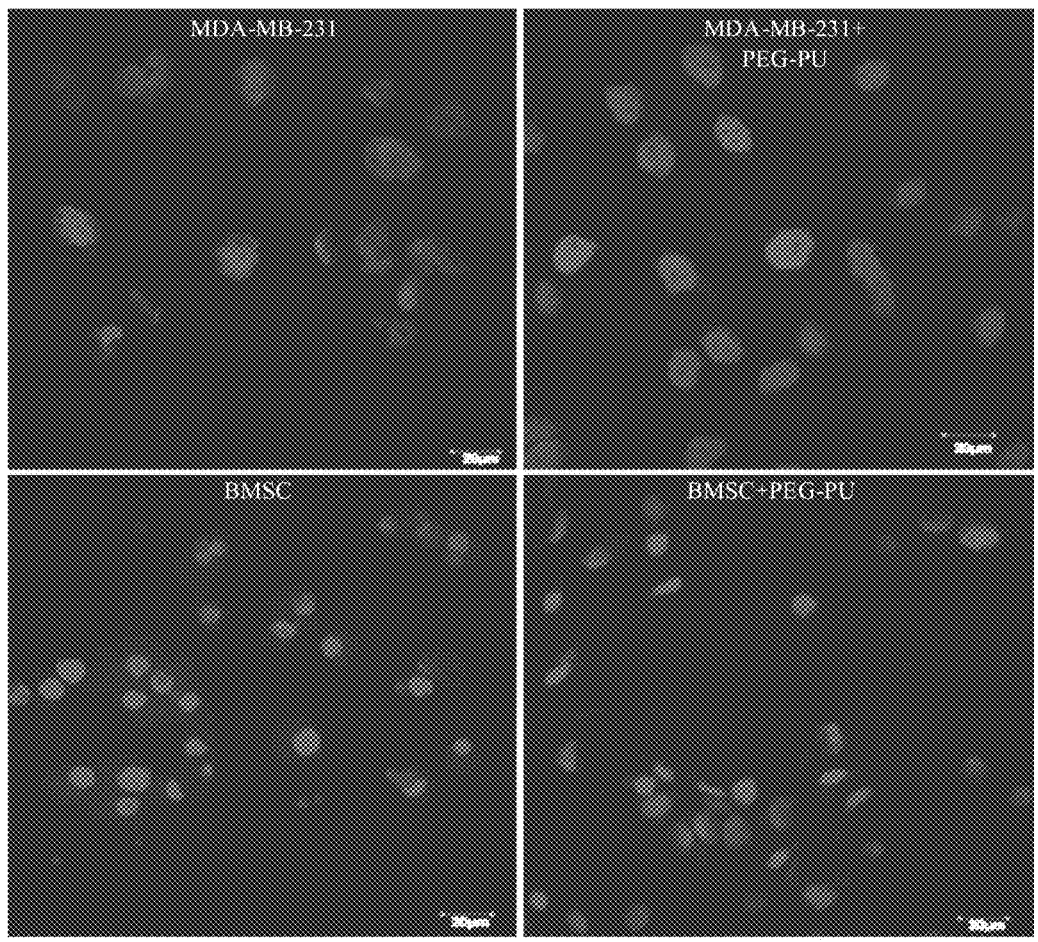

Encouragingly, MDA-MB-231 cells cultured with or without polymer networks did not depict any changes in cellular morphology (FIG. 2E). To corroborate the results of viability and cytotoxicity, finally we performed MTT assay and Hoechst staining to evaluate rate of proliferation and apoptosis of cells imparted by these polymer networks, respectively. There was no significant change in proliferation rate of either cell-lines as well as primary cells (FIG. 2F). Hoechst staining depicted relatively less apoptotic nuclei in presence of polymer indicating these to be non-cytotoxic and cytocompatible for MDA-MB-231 cell line (FIG. 2G upper panel) and BMSC (FIG. 2G lower panel). In the present study, we cultured two types of cell lines from various tissue origins like Breast adenocarcinoma (MDA-MB-231) and Human Liver adenocarcinoma (SK-Hep1). Although, the polymer network did not impart any cytotoxic effect on cell lines we further studied using primary BMSC isolated from the C57BL/6J mice to assess feasibility of using these polymers as delivery vehicles for cell transplantation. Thus these polymer networks indicate the feasibility of being used as cell carriers for primary cells, in any auto/allogenic cell transplantation therapies.

Example 5: Analysis of Cell Penetration in Polymer Networks

Figure 3A:
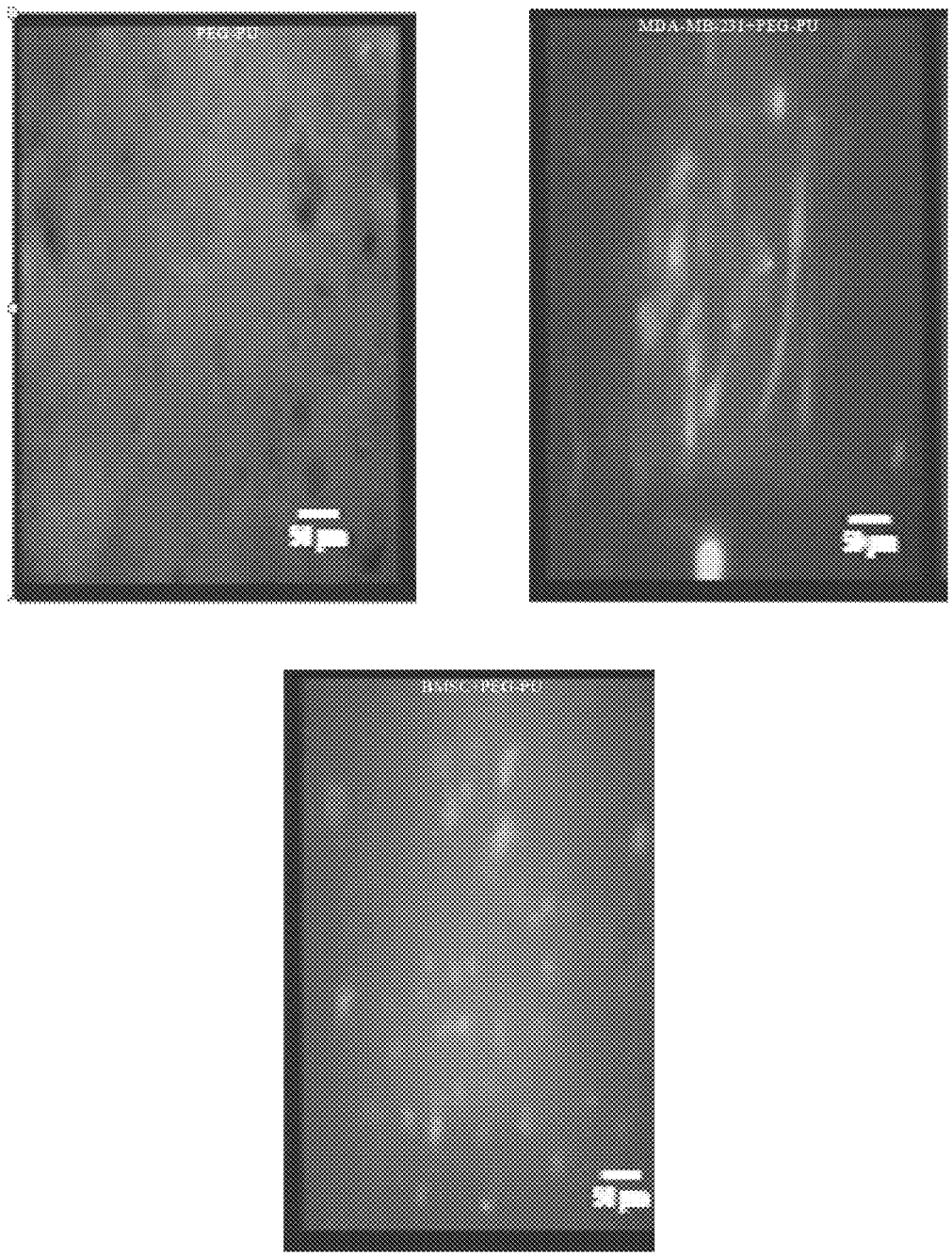
Figure 3B:
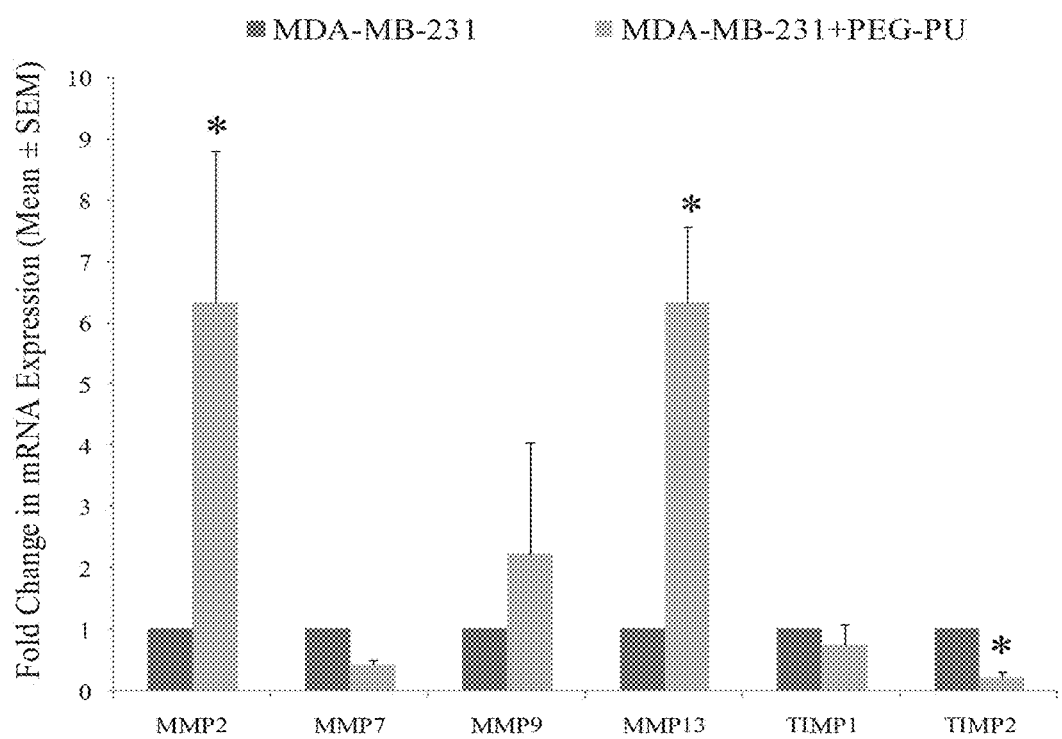
Figure 3C:
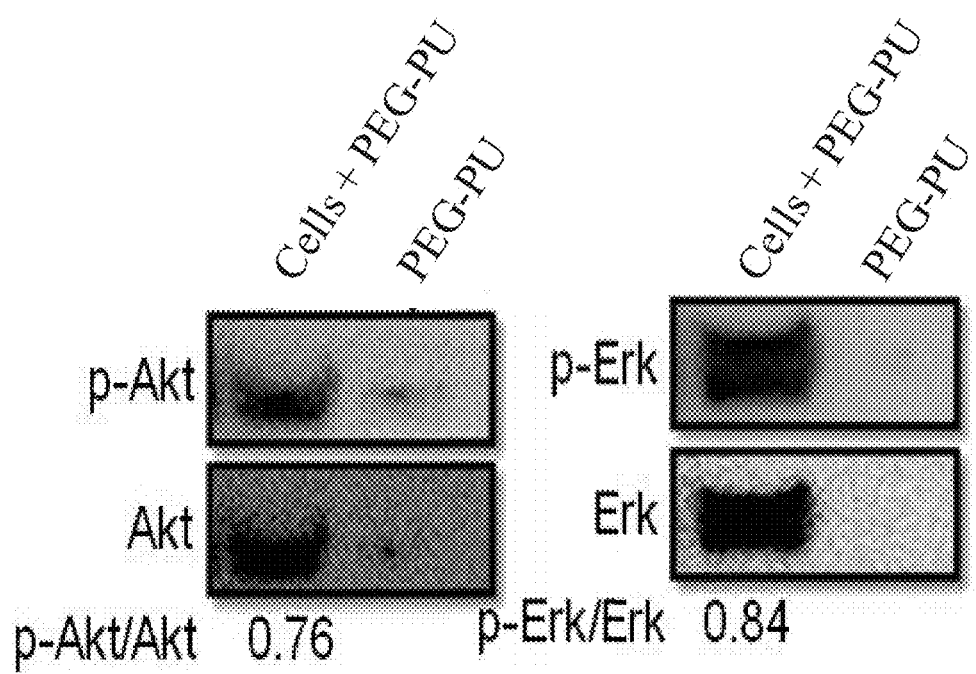
Figure 3D:
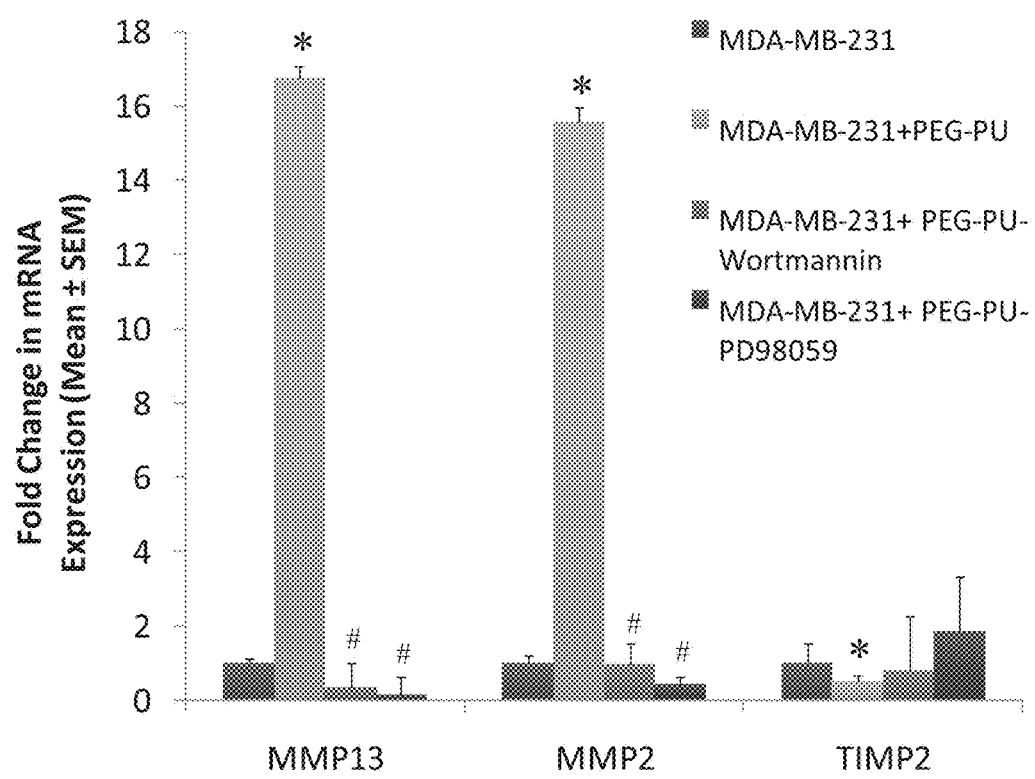
Figure 3E:
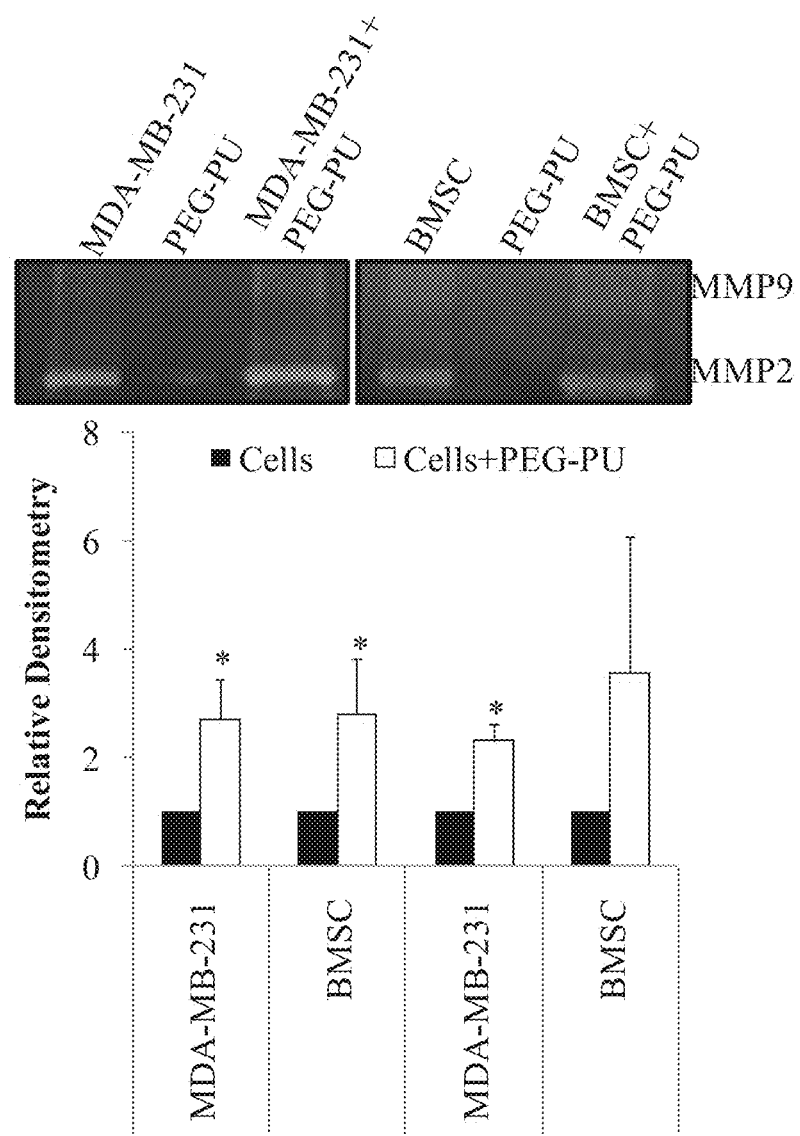
Figure 4A:
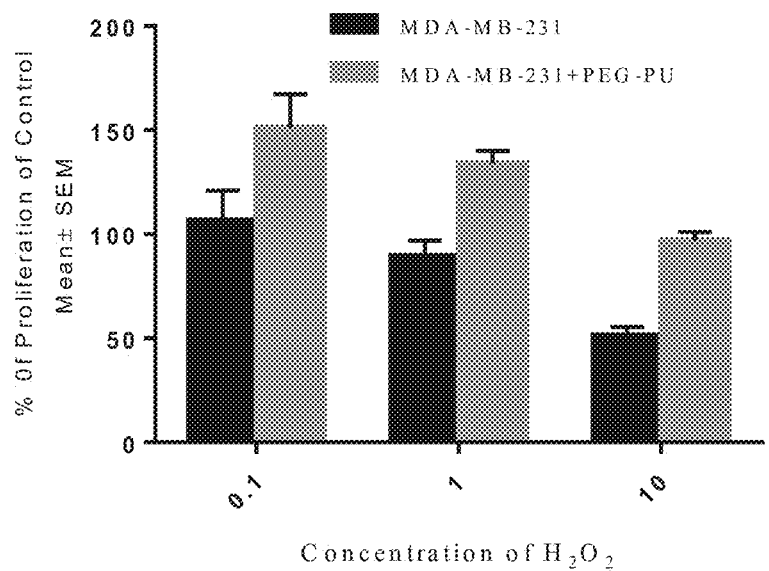
Figure 4B:
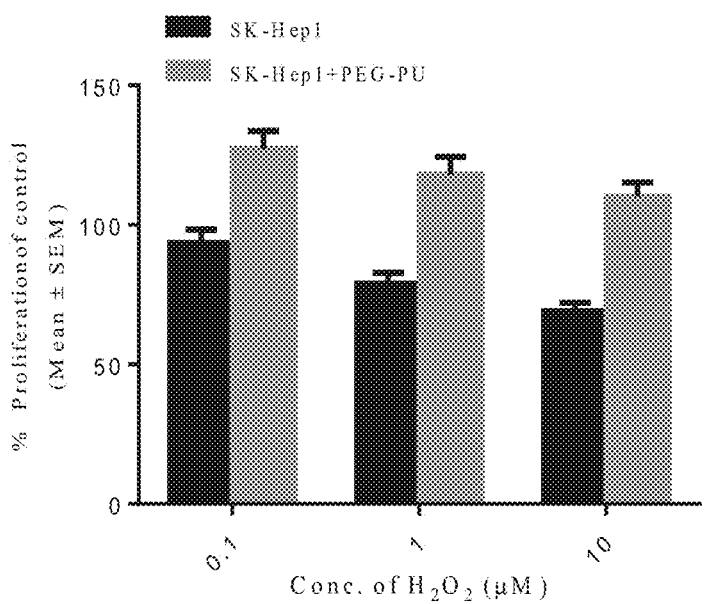
Figure 4C:
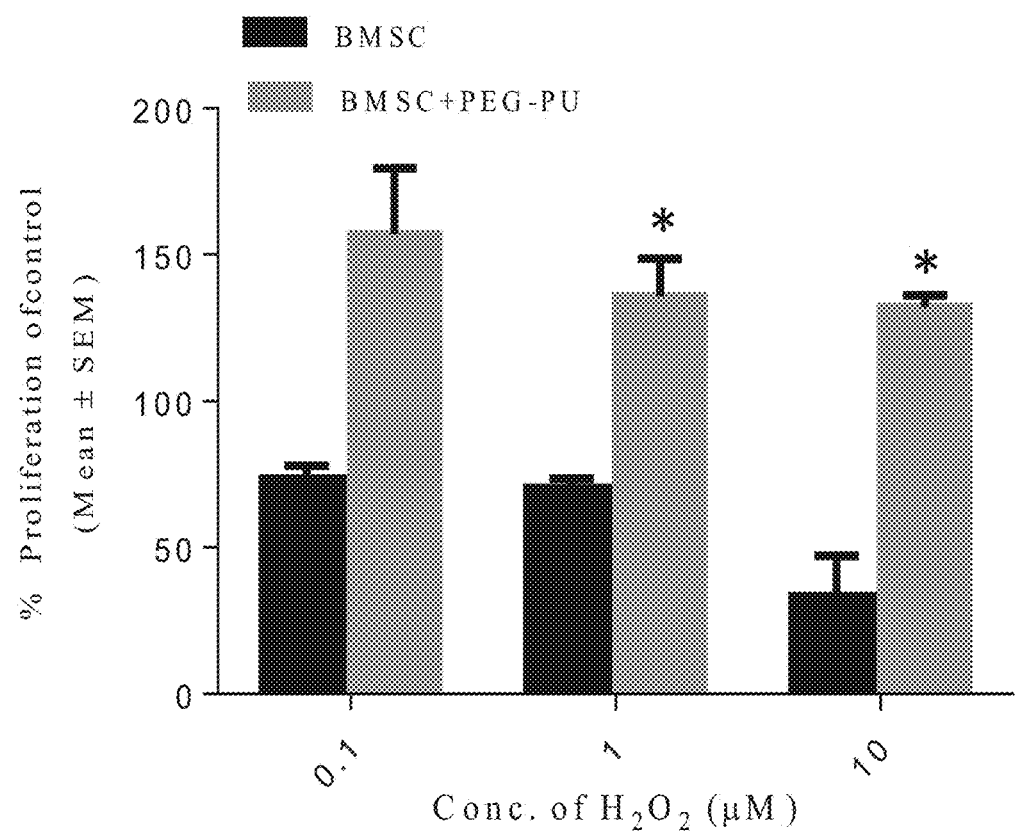
Figure 4D:
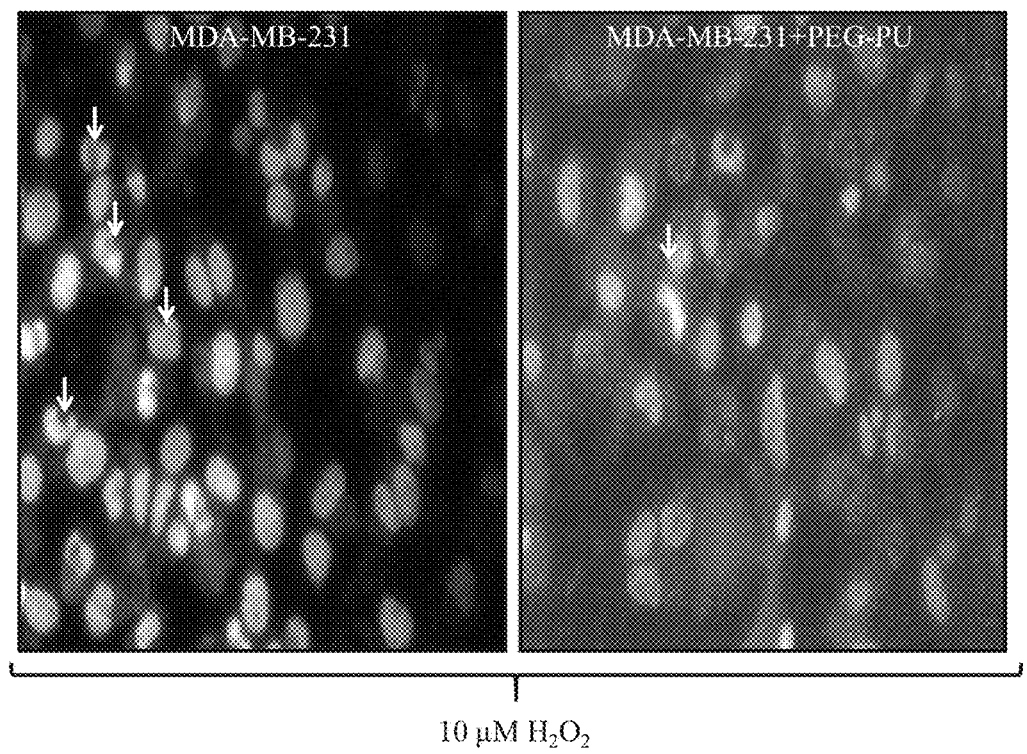
Figure 4E:
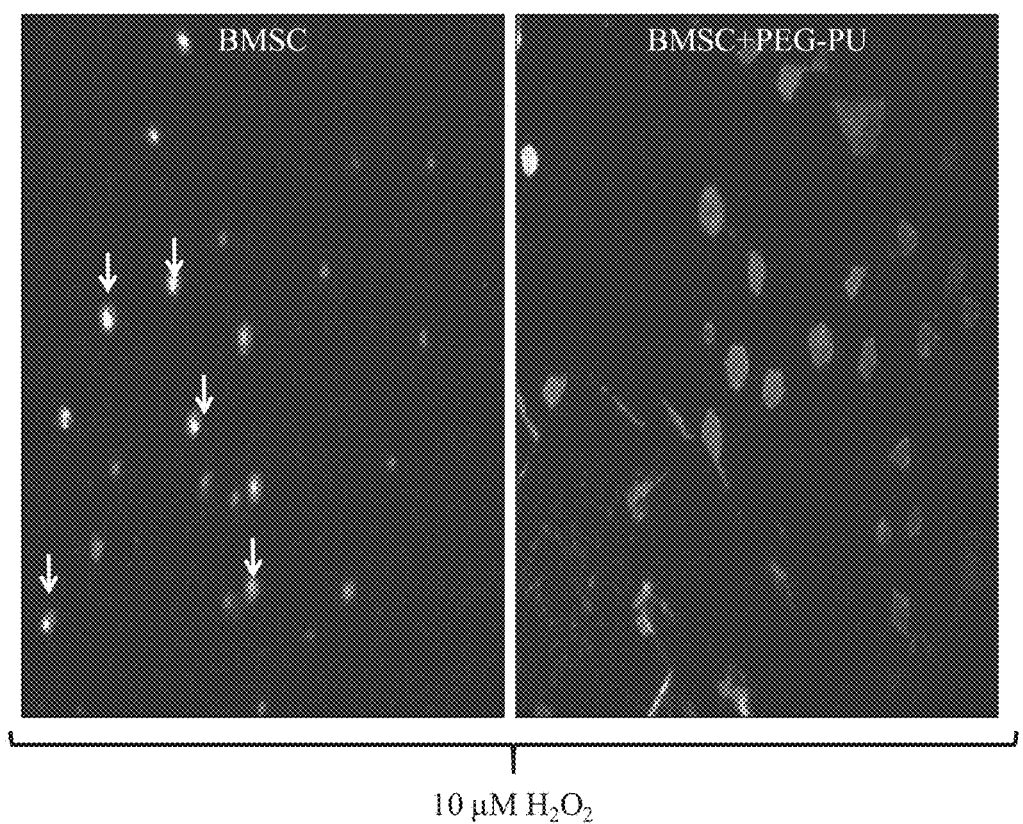

The polymers containing MDA-MB-231 and BMSCs were cut into 20 μm sections and stained with hematoxylin-eosin. Sections of control group i.e, polymer networks incubated with only medium (without cells) showed intact cross-linking of the polymer (FIG. 3A) whereas from experimental group i.e., polymer networks cultured with the cells depicted an architecture with degraded cross-linking along with concomitant appearance of cells (FIG. 3A; FIG. 11). This may be attributed to the action of proteases released by cells on polymer. We performed qPCR analysis for expression levels of matrix metallo-proteinases (MMPs) and TIMPs (tissue inhibitor of MMPs) in the polymer network-penetrated cells after clearing off surface attached cells. Incidentally, these cells as compared to control cells were observed to express 6-7-fold high MMP-13 (Collagenase 3) and MMP-2 (Gelatinase A) among other MMPs evaluated such as MMP-7 (Matrilysin), MMP-9 (Gelatinase B) along with a significant decrease in TIMP-2 and moderate decrease in TIMP-1 expression (FIG. 3B; FIG. 12). Furthermore, protein expression of phosphorylated Erk and phosphorylated Akt in cells penetrated the polymer network suggests an activation of Erk and Akt signaling-mediated MMP expression for cell migration (FIG. 3C). To validate these results MMP-13, MMP-2 and TIMP-2 mRNA expression was further evaluated in cells cultured in presence of polymers and treated with or without Wortmannin and PD98059, Akt and ERK inhibitors, respectively. A significant decrease (reversal) in expression of MMP-13 and MMP-2 in presence of pathway blockers confirms the involvement of Akt and Erk pathways in increased expression of these MMPs (FIG. 3D).

Example 6: Protective Effect from In Vitro Oxidative Stress by Polymer Networks

To mimic the pathological conditions, we set an experiment where cells were exposed to $H_2O_2$ at different concentrations of 0.1, 1 and 10 μM and cultured in presence and absence of polymer networks. A dose-dependent effect of oxidative stress on proliferation of MDA-MB-231 cells (FIG. 4A), SK-HEP1 cells (FIG. 4B) and BMSCs (FIG. 4C) was observed. However, cells cultured in presence of polymer scaffolds depicted a significant protection against the oxidative stress during proliferation. Furthermore, MDA-MB-231 cells (FIG. 4D) as well as BMSC (FIG. 4E) when cultured at high concentration of $H_2O_2$ (10 μM) depicted marked increase in apoptosis which was shielded when cultured in presence of polymer networks. Technically, the unsaturated chain segments in castor oil along with soft ether portion of polymers are sensitive to free radicals or oxidative degradation. Our polyethyleneglycol-polyurethane networks synthesized using castor oil hence protects the cells from oxidative stress as evident from results of proliferation and apoptosis studies, due to their inherent anti-oxidative properties.

Figure 5A:
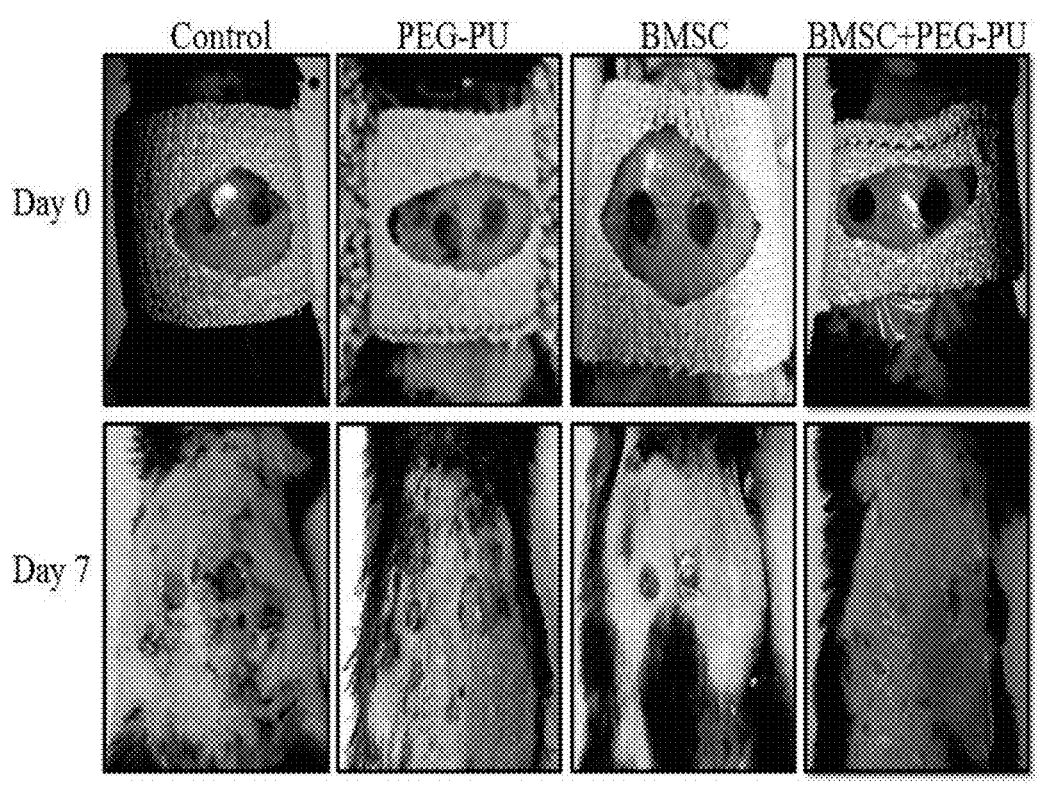
Figure 5B:
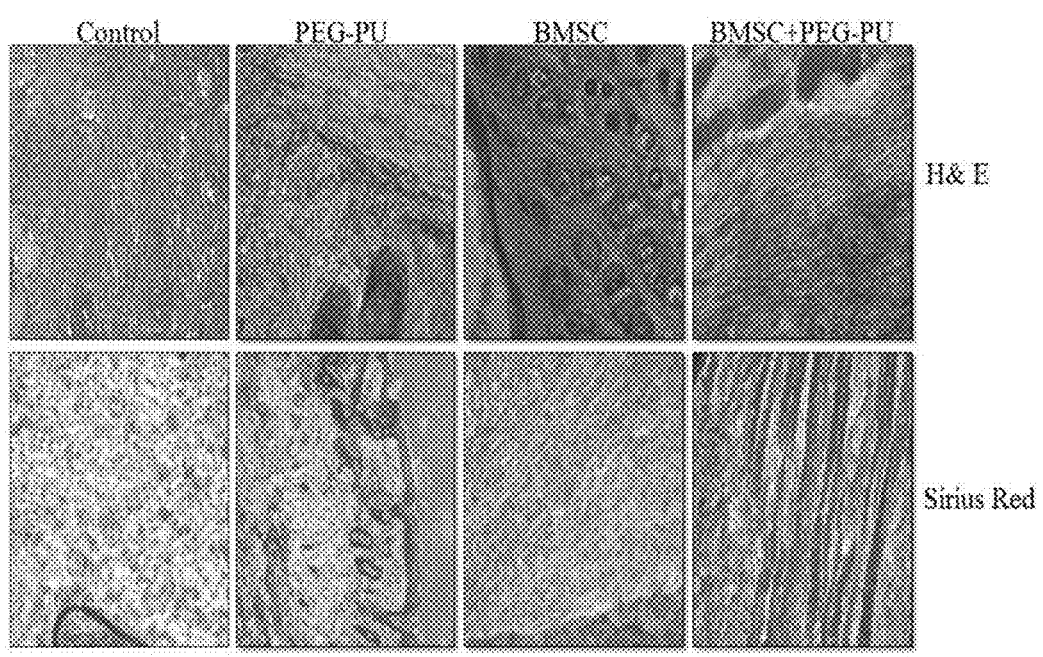
Figure 5C:
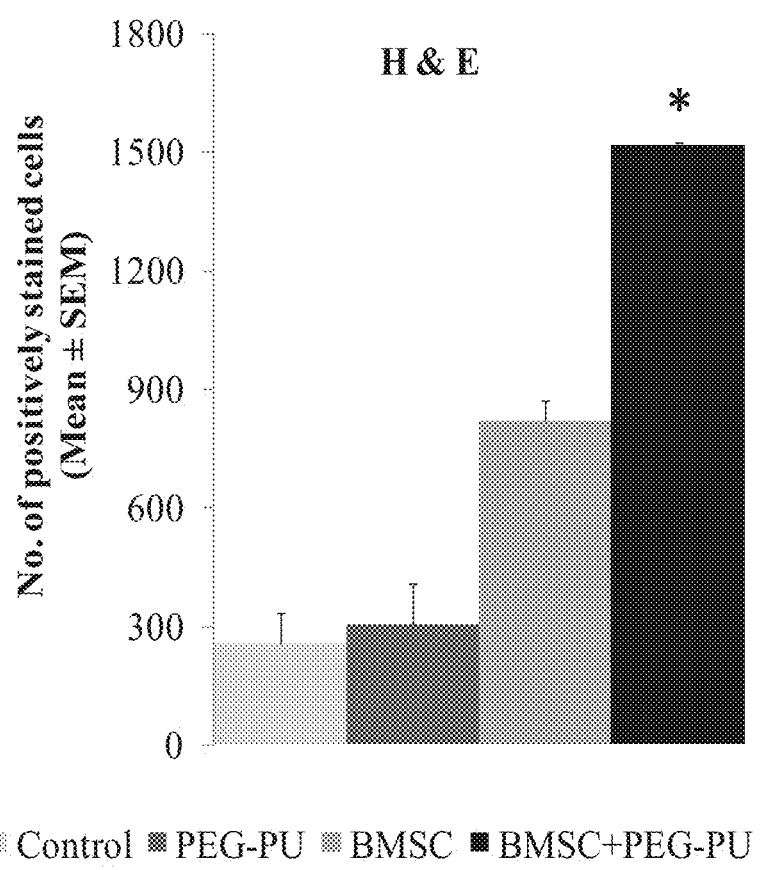
Figure 5D:
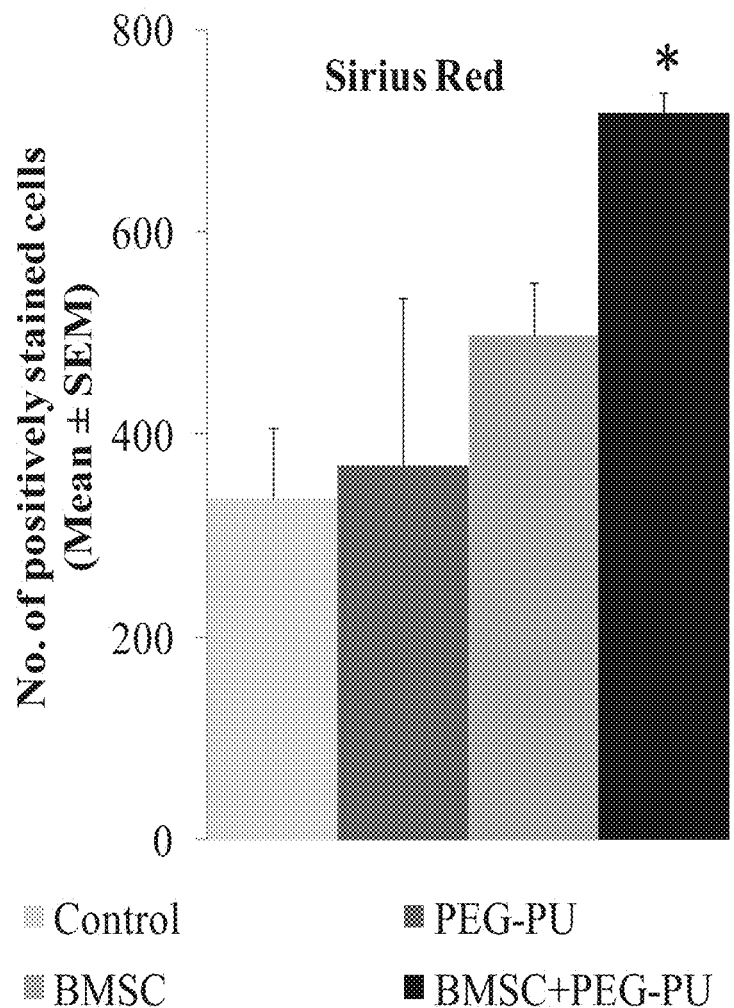

Example 7: Transplantation of BMSCs Using Polymer Networks at Excisional Splinting Wound Site To further confirm the anti-oxidant effect of polymer network in vivo, we developed a murine model of excisional splinting wound. In full excisional wounds, contraction accounts for the larger part of wound closure in rodents. In splint model, a silicon ring was adhered around the wound tightly preventing contraction and heals through granulation and re-epithelization that occurs in humans. Wound healing in mouse often requires 14 days in an excisional splinting wound model. We transplanted equal number of BMSCs derived from C57BL/6J mice into excisional wounds in syngenic mice which were cultured in presence or absence of polymer network (FIG. 15). Mice implanted with BMSC-polymer network (BMSC+PEG-PU) exhibited an accelerated wound closure at post-surgery day 7 as compared to mice transplanted with BMSCs (FIG. 5A). This enhanced wound healing in BMSC-polymer network group as compared to BMSCs was more evident when evaluated at post-surgery day 10 (FIG. 13). From histopathology studies, it was evident that at post-surgery day 7, proliferation of fibroblasts was higher in the BMSC-polymer network implanted wounds as depicted by Hematoxylin-Eosin staining (FIG. 5B). Deposition of collagen was also markedly increased in BMSC-polymer network implanted wounds depicting the acceleration of wound healing as early as in post-surgery day 7 (FIG. 5B). Quantitative analysis using Image J software depicted a significant increase in fibroblast (FIG. 5C) and collagen presence in BMSC-polymer network group (FIG. 5D). A similar increased fibroblasts and collagen deposition was observed at post-surgery day 10 (FIG. 14).

Figure 5E:
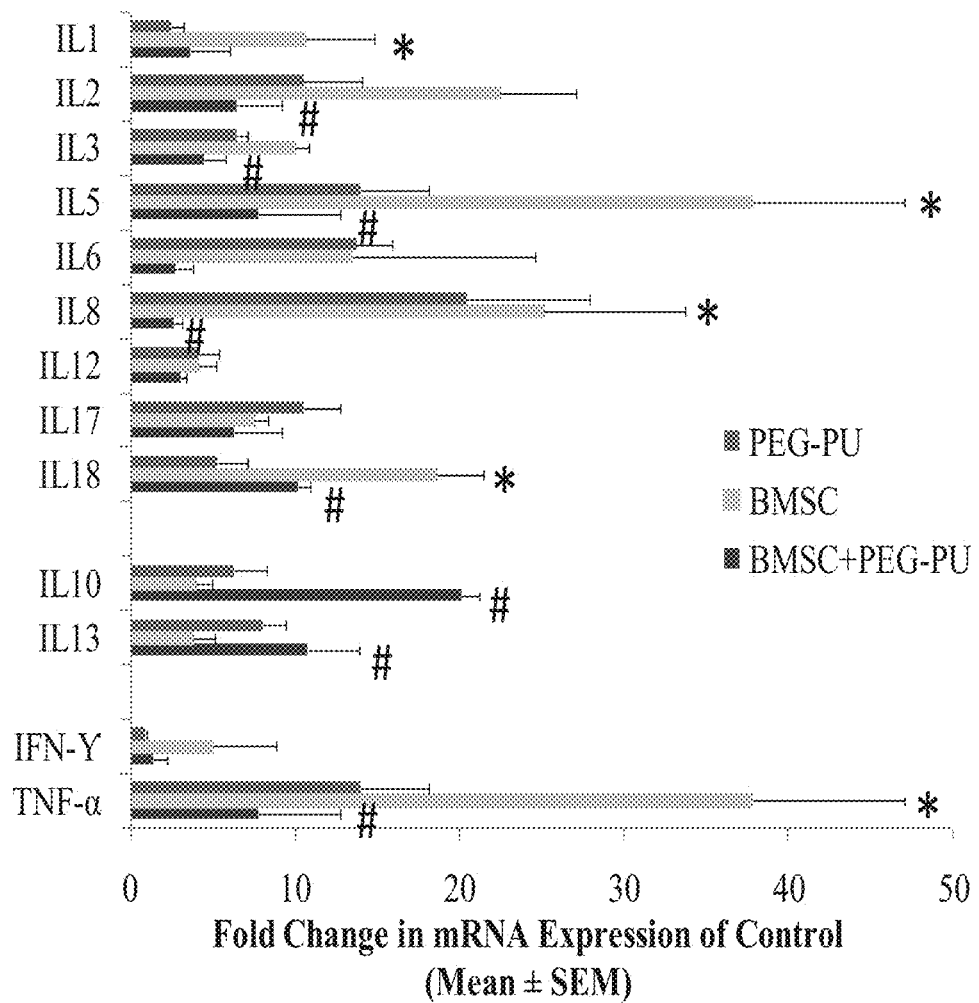

Example 8: Protection from Inflammatory Cytokines at Wound Site by Polymer Network To investigate the role of inflammatory cytokines at wound site in our excisional splinting wound model that regulates rate of healing, we performed a qPCR analysis for expression levels of a panel of cytokines at a post-surgery day 7. The mRNA expression levels of pro-inflammatory cytokines such as IL1β, IL2, IL3, IL5, IL6, IL8, IL18 and TNF-α were significantly up-regulated in the BMSC transplanted group as compared to both vehicle control (PEG-PU) and BMSC-polymer network (BMSC+PEG-PU) transplanted wounds. Furthermore, a significant decrease in expression of selected key pro-inflammatory cytokines that often regulates the wound healing, IL1β, IL6, IL8 and TNF-α was observed in BMSC-polymer network as compared to BMSC-transplanted mice. Interestingly, the expression of anti-inflammatory cytokines, IL10 and IL13 were significantly up-regulated in BMSC-polymer network transplanted wound site (FIG. 5E). These results indicate protective property of polymer network in balancing the inflammatory cytokines by down-regulating pro-inflammatory and up-regulating anti-inflammatory cytokines which contributes to enhanced wound healing.

Example 9: Protection from Oxidative Stress at Wound Site by Polymer Networks

Figure 6A:
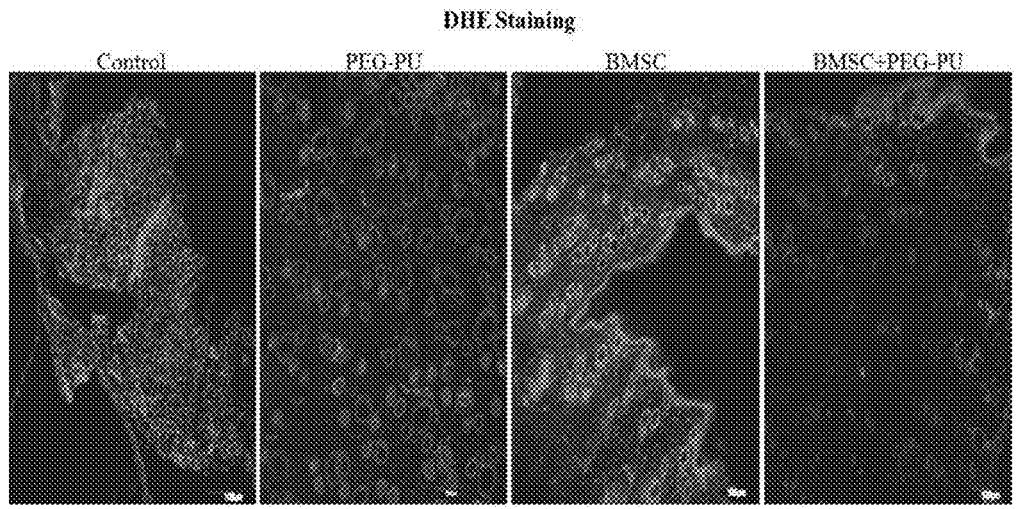
Figure 6B:
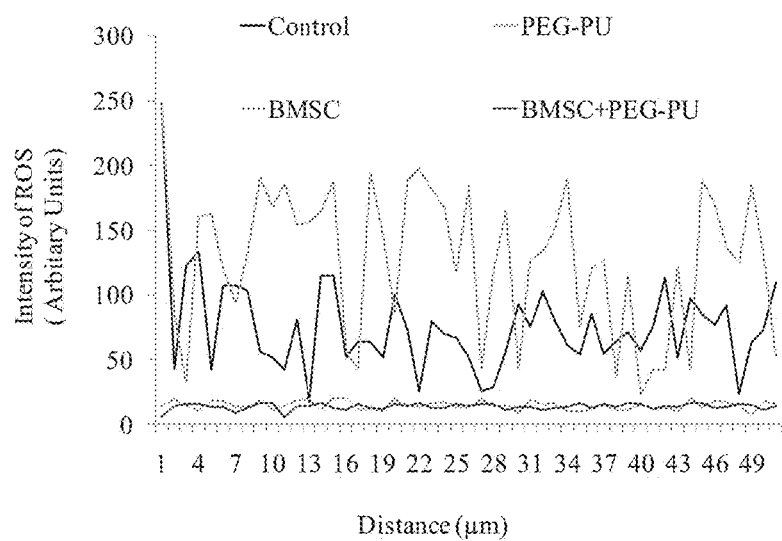
Figure 6C:
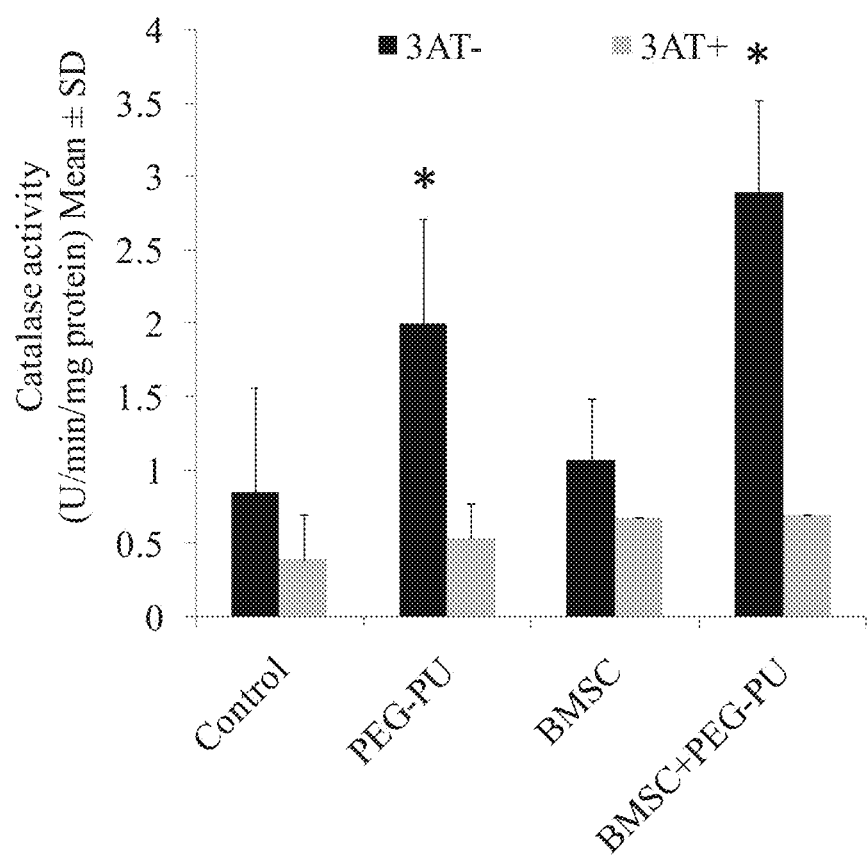
Figure 6D:
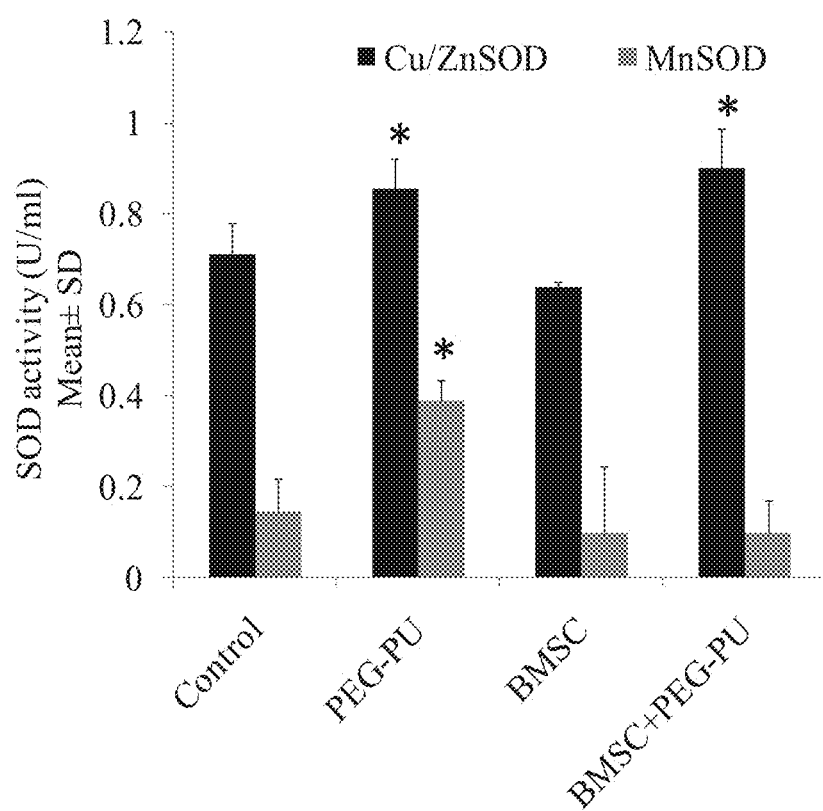
Figure 6E:
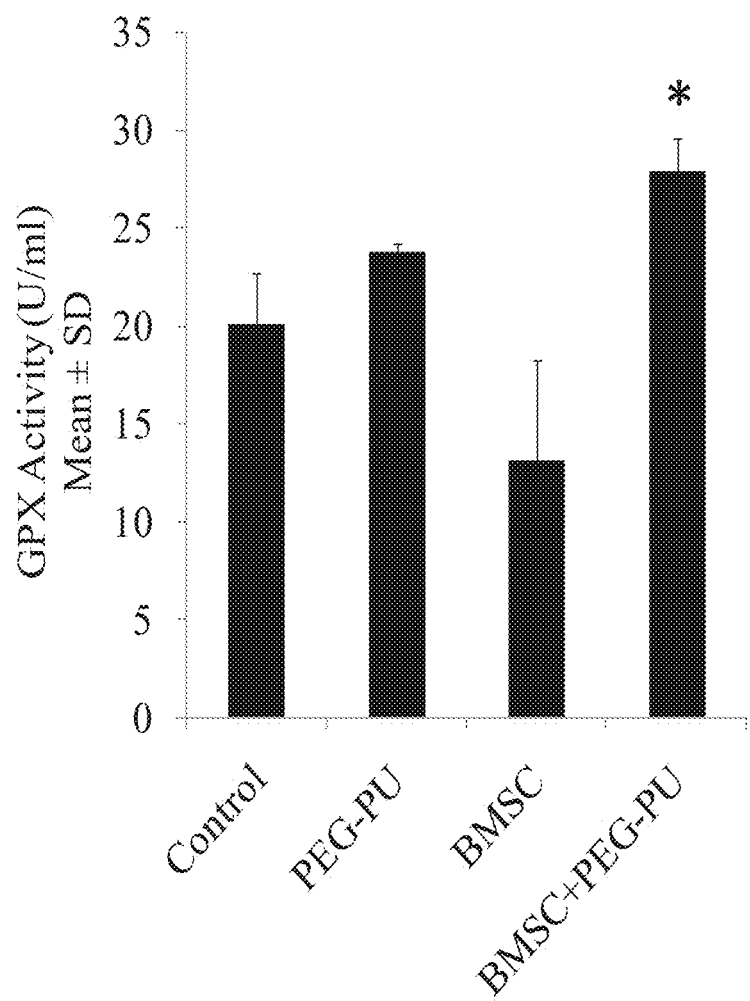
Figure 6F:
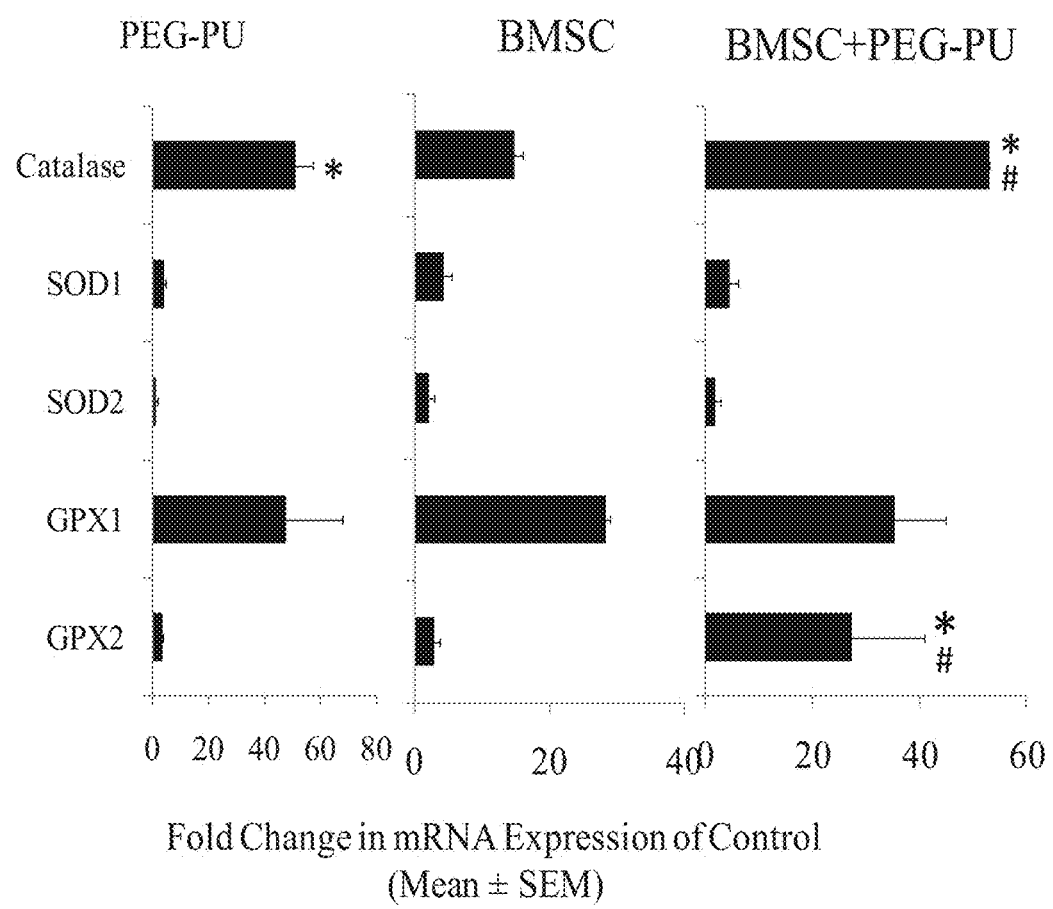

Thus in events of cell transplantation to such diseased tissue microenvironment, ROS-induced apoptosis of transplanted cells can be avoided by using a suitable cell delivery scaffold which will shield the oxidative stress effect. In order to further confirm a protective role of our polymer network from the oxidative stress generated at the wound site, levels of ROS and antioxidant enzyme activities were determined. The levels of ROS were significantly higher in control wound and BMSC-transplanted wounds as compared to both vehicle control and BMSC-polymer network transplanted wounds (FIG. 6A). Quantification revealed an increased ROS levels in BMSC treated wounds as compared to the control wounds (FIG. 6B) suggesting an increased oxidative stress confronted by the transplanted cells. To further corroborate the decreased ROS levels in presence of polymer network we investigated activities of anti-oxidant enzymes. A significant increase was observed in the Catalase activity (≥3.4 fold) (FIG. 6C) and Cu/Zn-SOD or SOD1 (≥1.2 fold) but not Mn-SOD or SOD2 (FIG. 6D) in both vehicle control and BMSC-polymer network treated wounds. However, GPx (second line of defense) activity was 1.3 fold high in only BMSC-polymer network transplanted wounds (FIG. 6E). Additionally, to investigate if the enhanced anti-oxidant enzyme activities at the wound site in presence of polymer networks are regulated at their protein or mRNA levels, we performed qPCR analysis of these anti-oxidant enzyme genes. Results revealed a significant increase in the expression of catalase, cytoplasmic SOD1, GPx2 thereby correlating with the enhanced activity of these enzymes at the wound site of BMSC-polymer network transplanted mice as compared to other groups (FIG. 6F).

The process of wound healing necessitates equilibrium between increased ROS levels and enzymatic/non-enzymatic antioxidants. Any imbalance would result in delayed wound healing and unsuccessful tissue regeneration (See, Bryan, N. et al., J. A. Eur. Cells and Mater. 2012, 24, pp. 249-65). Our findings are in alignment with the increase in ROS and depletion in antioxidant levels of control wound post-surgery day 7. Depletion in ROS levels in vehicle control treated wounds also correlates well with our in vitro results thereby confirming the anti-oxidant property of polymer network. Also literature suggests supplementation of vitamin E has shown an increased levels of SOD, catalase and GPx activities accelerating the rate of wound closure (See, Musalmah, M. et al., *Plastic & Reconstructive Surg.*, 1997, 100, pp. 1901-1902). Interestingly, our scaffolds synthesized from castor oil, a rich source of vitamin E has depicted an increase in activity and gene expression levels of catalase, Cu/Zn SOD, GPx activities in vehicle control and BMSC-polymer network treated wounds. The activity of cytoplasmic Cu/ZnSOD was significantly higher in both PEG-PU treated wounds with and without cells, which may be attributed to its constitutive expression in cells unlike MnSOD, an inducible that often does not express in anaerobic conditions (See, Sun, W. *Free Rad. Biol. Med.* 2011, 77, p. 222). These observations strongly suggest that our polymer network retains its significant anti-oxidant property in vivo as well, imparting a protective role.

Example 10: Enhanced Engraftment of BMSCs at Wound Site by Polymer Networks

To examine engraftments of BMSCs into the wound, we performed immunofluorescence analysis of tissue sections for selective stem cell markers such as CD133 and CD90.2 using confocal microscopy. At post-surgery day 7 as compared to the mice group transplanted with BMSCs, abundant BMSCs were found throughout the regenerated wound tissue in mice implanted with BMSC-polymer network (FIG. 7A). Further quantitative analysis evidently revealed a ≥3.5-fold increase in number of positively stained cells in BMSC-polymer network group (FIG. 7B). An increased engraftment of BMSCs (CD90$^+$CD133$^+$) resulted in decrease of wound closure time by 58.33%. However, at post-surgery day 10 similar levels of engrafted BMSCs were observed in the regenerated wound tissues of BMSC-polymer network and BMSC transplanted groups (FIG. 7B and FIG. 16). Our results are in parallel with a recent study depicting a decrease in the number of BM-MSCs after intramyocardial injection during acute myocardial infarction at a later phase of the tissue regeneration (See, Noiseux, N. et al., *Mol. Ther.* 2006, 14, pp. 840-850).

Example 11: Enhanced Neo-Vascularization During Wound Repair by Polymer Networks Neo-vascularization is a crucial and essential phase involved in remodeling of the tissue regeneration (See, Wu, Y. et al., *Stem Cells* 2007, 25, pp. 2648-2459). Finally, accelerated wound healing by BMSCs in presence of polymer network was evaluated in terms of increased vascularity. Regenerated wound tissue sections at post-surgery day 7 (FIG. 8A) and day 10 (FIG. 8A) depicted an enhanced staining of endothelial cells-specific protein markers CD31 in BMSC-polymer network group as compared to only BMSC transplanted and vehicle control groups. The immunofluorescence staining quantified as described in methods depicted a 2-2.5-fold increase in BMSC-polymer network implanted group as compared to BMSCs transplantation group (FIG. 8B). To further confirm the neo-vascularization in BMSC-polymer network group, mRNA expression levels of several endothelial cell-specific receptors, (VEGFR1, VEGFR2 and VEGFR3) and co-receptors (Nrp1, Nrp2) were quantified using qPCR analysis. Results have shown a significant increase in the expression of VEGFR2, VEGFR3 and Nrp2 in BMSC-polymer network transplanted wounds at post-surgery day 7 (FIG. 8C). Also Tie-2, a specific marker for neo-vascularization was significantly up-regulated in BMSC-polymer network implanted wounds. Thus these results confirmed the accelerated wound healing by BMSC-polymer network transplantation via increased neo-vascularization.

Our studies suggest that castor oil based polyethyleneglycol-polyurethane networks (FIG. 9A) are satisfactorily biocompatible with wide variety of cells as well as pH-sensitive and enzymatically biodegradable. Cellular penetration of these porous polymer networks were evident by increased expression of selective MMPs and Akt/Erk activation. Oxidative stress-mediated cellular apoptosis and decreased proliferation was abrogated by the presence of these polymer networks (FIG. 9B). Protection from oxidative stress and inflammation, enhanced engraftment of BMSCs at wound site with increased neo-vascularization accelerated wound repair process (~50% faster) as early as post-surgery day 7 (FIG. 9C). Therefore, these polymers can serve as suitable cell delivery vehicle or scaffolds for tissue engineering in stem cell transplantation therapies.

Having now fully described this invention, it will be understood by those of ordinary skill in the art that the same can be performed within a wide and equivalent range of conditions, formulations and other parameters without affecting the scope of the invention or any embodiment thereof. Accordingly, the present embodiments are to be considered as illustrative and not restrictive, and the inventions is not to be limited to the details given herein, but may be modified within the scope and equivalents of the appended claims.

ADVANTAGES OF THE INVENTION

The main novelty of the invention lies in the use of polyethylene glycol-polyurethane as the matrix for stem cell delivery. The formulation to achieve the right compositions of polyethylene glycol-polyurethane remains the inventive step to achieve the claimed porosity, anti-oxidant property and cell viability in these matrices. Specifically our inventiveness lies in preparing a scaffold formulation that can use (i) these porous polyethylene glycol-polyurethane polymers as effective cell delivery vehicle at injury site; (ii) use of castor oil in the framework to impart anti-oxidative properties to the scaffolds; (iii) enzymatically biodegradable and biocompatible properties (iv) reduction of inflammatory cytokines, enhancement of engraftment of stem cells, and increase in neo-vascularization at the injury site.

The other advantages are:
  The porous polymer scaffold possesses high thermo and barostability, biodegradability, biocompatibility.
  The porous polymer scaffold accelerates wound healing via increased neo-vascularization.
  The castor oil based PEG-PU networks are pH-sensitive and enzymatically biodegradable.
  The porous polymer scaffolds shield the oxidative stress effect and thereby avoiding ROS-induced apoptosis of transplanted cells.
  The porous polymer scaffold balances the inflammatory cytokines by down-regulating pro-inflammatory and up-regulating anti-inflammatory cytokines which contributes to enhanced wound healing.

We claim:

1. A porous polymer scaffold for tissue engineering in stem cell transplantation consisting of a crosslinker, where the crosslinker comprises castor oil, polyether backbone, an isocyanate containing compound, and a secondary component, wherein the scaffold has a pore size that ranges from 50 nm-5 µm.

2. The porous polymer scaffold of claim 1, wherein the crosslinker is a triglyceride of castor oil.

3. The porous polymer scaffold of claim 1, wherein the polyether backbone is selected from the group consisting of di-hydroxyl, di-amine, and di-carboxyl terminated compounds.

4. The porous polymer scaffold of claim 1, wherein the polyether backbone is selected from the group consisting of polyethylene glycol (PEG), polypropylene glycol (PPG), polytetramethylene glycol (PTMG), block copolymers thereof, branched/graft copolymers thereof, and combinations thereof.

5. The porous polymer scaffold of claim 4, wherein the polyether backbone is polyethylene glycol (PEG) with molecular weight of 400-10000 Daltons.

6. The porous polymer scaffold of claim 1, wherein the isocyanate containing compound is selected from the group consisting of methylene diphenylene diisocyanate (MDI), polymeric methylene diphenylene diisocyanate (p-MDI), toluene diisocyanate (TDI), hexamethylene diisocyanate (HMDI), dicyclohexane methylene diisocyanate (H12MDI), isophoronediisocyanate (IPDI), xylene diisocyanate, hydrogenated xylene diisocyanate, and Desmodur-N.

7. The porous polymer scaffold of claim 1, wherein the secondary component is polyethylene glycol dimethylether of average molecular weight 250, 500, 750, 2000 or 5000 Daltons.

8. The porous polymer scaffold of claim 7, wherein the secondary component is polyethylene glycol dimethylether of average molecular weight 500 Daltons.

9. A process to prepare the porous polymer scaffold of claim 1, wherein the process comprises:
  (a) reacting Castor oil (10 wt % to 60 wt % of total reactant weight) with diphenylmethane-4,4'-diisocyanate (with total —NCO/—OH ratio in the range of 0.8-2.5) in tetrahydrofuran (THF) as solvent for 1 hour to form a pre-polymer (stage-I);
  (b) charging the pre-polymer (stage-I) as obtained in step (a) with polyether macromonomer, N, N-dimethylaniline, and additional THF to obtain charged pre-polymer;
  (c) adding a catalyst to the charged pre-polymer obtained in step (b) at room temperature to initiate the formation of a polyethylene glycol-polyurethane (PEG-PU), component-I (stage-II) and to obtain a growing polymer network;
  (d) adding polyethylene glycol dimethylether (PEGDME) to the growing polymer network of step (c) to obtain a reaction mixture;
  (e) degassing and vigorously mixing the reaction mixture as obtained in step (d) under inert atmosphere to obtain a uniformly homogeneous viscous mix;
  (f) casting the uniformly homogeneous viscous mix as obtained in step (e) onto a teflon petri-dish to obtain a polymeric product;
  (g) drying the polymeric product as obtained in step (f) at room temperature for 24 h followed by curing at higher temperature and inert atmosphere at 60-90° C. for 48 h-96 h forming a semi-IPN matrix;
  (h) wrapping free standing films of the semi-IPN matrix as obtained in step (g) in Whatman filter paper bag and exposing to a repeated soxhlet extraction process to obtain processed films;
  (i) subjecting the processed films as obtained in step (h) to repeated swelling and drain cycles for 4-7 days against THF to extract out the PEGDME from the semi-IPN matrix completely, leaving behind a porous polymer network scaffold with impurities; and (j) continuing extraction on the porous polymer network scaffold with impurities for 2 days using deionized millipore water (18MΩ) to obtain an impurity free and sterile porous polymer scaffold.

10. The process of claim 9, wherein the castor oil in step (a) is 40% of the total reactant weight.

11. The process of claim 9, wherein the —NCO/—OH ratio of diphenylmethane-4,4'-diisocyanate is in the range of 1.2 to 1.4.

12. The process of claim 9, wherein the polyether macromonomer in step (b) is polyethylene glycol (PEG).

13. The process of claim 12, wherein the polyethylene glycol (PEG) in step (b) is in the range of 70 wt % to 30 wt % of total weight.

14. The process of claim 9, wherein the THF in steps (a) and (b) is in the range of 20 wt % to 30 wt % of solids during reaction.

15. The process of claim 9, wherein the N, N-dimethylaniline in step (b) is in the range of 0.1 wt % to 2 wt % of solid content.

16. The process of claim 9, wherein the catalyst in step (c) is a tertiary amine.

17. The process of claim 16, wherein the tertiary amine is dimethylaniline (DMA).

18. The process of claim 9, wherein the polyethylene glycol dimethylether (PEGDME) in step (d) has a non-reactive end group and is used in the range of 20 wt % to 70 wt % of total weight of component-I.

19. The process of claim 18, wherein the polyethylene glycol dimethylether (PEGDME) is used in the weight ratio (50:50).

20. A method of treating tissue damage and expediting wound tissue regeneration and repair, wherein the method comprises administering to a subject a composition comprising the porous polymer scaffold of claim 1.

* * * * *